United States Patent
Chiu et al.

(10) Patent No.: US 9,040,057 B2
(45) Date of Patent: May 26, 2015

(54) METHOD OF DIAGNOSING AND PREVENTING PNEUMOCOCCAL DISEASES USING PNEUMOCOCCAL NEURAMINIDASES

(75) Inventors: Cheng-Hsun Chiu, Taoyuan (TW); Rajendra Prasad Janapatla, Taoyuan (TW); Chyi-Liang Chen, Taoyuan (TW); Mei-Hua Hsu, Taoyuan (TW); Hsiu-Ling Chen, Taoyuan (TW); Chung-Tsui Huang, Taoyuan (TW); Hsin-Ju Chang, Taoyuan (TW); Wan-Ting Liao, Taoyuan (TW)

(73) Assignee: CHANG GUNG MEDICAL FOUNDATION, LINKOU BRANCH, Taoyuan (TW)

( * ) Notice: Subject to any disclaimer, the term of this patent is extended or adjusted under 35 U.S.C. 154(b) by 150 days.

(21) Appl. No.: 13/244,482

(22) Filed: Sep. 25, 2011

(65) Prior Publication Data

US 2013/0078259 A1  Mar. 28, 2013

(51) Int. Cl.
*A61K 39/00* (2006.01)
*A61K 39/02* (2006.01)
*A61K 39/09* (2006.01)
*A61K 39/085* (2006.01)
*G01N 33/573* (2006.01)

(52) U.S. Cl.
CPC ............ *A61K 39/092* (2013.01); *G01N 33/573* (2013.01); *G01N 2333/924* (2013.01); *G01N 2500/02* (2013.01); *A61K 2039/505* (2013.01)

(58) Field of Classification Search
CPC . A61K 2300/00; A61K 38/00; A61K 38/005; A61K 39/02; A61K 39/09; A61K 39/092; C07K 14/315
See application file for complete search history.

(56) References Cited

U.S. PATENT DOCUMENTS

2007/0286866 A1* 12/2007 Van Ginkel et al. ....... 424/164.1

OTHER PUBLICATIONS

Xu et al., (Acta Crystallogr Sect F Struct Biol Commun. 2008. 64(Pt 9):772-775).*

* cited by examiner

*Primary Examiner* — Ja'an Hines

(57) ABSTRACT

A method of providing protection against pneumococcal infection in a subject is disclosed. The method includes steps of administering to the subject a composition that includes combination of three recombinant pneumococcal neuraminidases: NanA, NanB, and NanC of *S. pneumoniae* strains CGSP14, wherein administration of the recombinant pneumococcal neuraminidases elicits an immune response to *S. pneumoniae*, and treats the subject. In one embodiment, the method further includes a step of adding adjuvants to enhance the immune response. The method also includes a step of using passive antibodies, wherein said passive antibodies are anti-neuraminidase antibodies generated from neuraminidases-immunized humanized animals: NanA, NanB, and NanC. Meanwhile, this invention also provides a method for the molecular diagnosis of pneumococcal infection.

5 Claims, 14 Drawing Sheets

SEQUENCE LISTING

<160> NUMBER OF SEQ ID NOS: 6

<210> SEQ ID NO 1
<211> LENGTH: 2943
<212> TYPE: DNA
<213> ORGANISM: Streptococcus pneumoniae strain CGSP14

<400> SEQUENCE: 1

| | | | | | |
|---|---|---|---|---|---|
| atgtcttatt | tcagaaatcg | ggatatagat | atagagagga | tcagtatgaa | tcggagtgtt | 60 |
| caagaacgta | agtgtcgtta | tagcattagg | aaactatcgg | taggagcggt | ttctatgatt | 120 |
| gtaggagcag | tggtatttgg | aacgtctcct | gttttagctc | aagaagggc | aagtgagcaa | 180 |
| cctctggcaa | atgaaactca | actttcgggg | gagagctcaa | ccctaactga | tacagaaaag | 240 |
| agccagcctt | cttcagagac | tgaactttct | ggcaataagc | aagaacaaga | aaggaaagat | 300 |
| aagcaagaag | aaaaaattcc | aagagattac | tatgcacgag | atttggaaaa | tgtcgaaaca | 360 |
| gtgatagaaa | aagaagatgt | tgaaaccaat | gcttcaaatg | tcagagagt | tgatttatca | 420 |
| agtgaactag | ataaactaaa | gaaacttgaa | aacgcaacag | ttcacatgga | gtttaagcca | 480 |
| gatgccaagg | ccccagcatt | ctataatctc | ttttctgtgt | caagtgctac | taaaaaagat | 540 |
| gagtacttca | ctatggcagt | ttacaataat | actgctactc | tagaggggcg | tggttcggat | 600 |
| gggcaacagt | tttacggtaa | ttacaacgat | gcacccttaa | aagttaaacc | aggtcagtgg | 660 |
| aattctgtga | cttcacagt | tgaaaaccg | acagcagaac | tacctaaagg | ccgagtgcgc | 720 |
| ctctacgtaa | acgggtatt | atctcgaaca | agtctgaaat | ctggcaattt | cattaaagat | 780 |
| atgccagatg | taacgcatgt | gcaaatcgga | gcaaccaagc | gtgccaacaa | tacggtttgg | 840 |
| gggtcaaatc | tacagattca | gaatctcact | gtgtataatc | gtgctttaac | accagaagag | 900 |
| gtacaaaaac | gtagtcaact | ttttaaacgc | tcagatttag | aaaaaaact | acctgaagga | 960 |
| gcggttttaa | cagagaaaac | ggacatattc | gaaagcgggc | gtaacggtaa | accaaataaa | 1020 |
| gatggaatca | agagttatcg | tattccagca | cttctcaaga | cagataaagg | aactttgatc | 1080 |
| gcaggtgcag | atgaacgccg | tctccattcg | agtgactggg | gtgatatcgg | tatggtcatc | 1140 |
| agacgtagtg | aagataatgg | aaagacatgg | ggagataagg | tggttatctc | caatcttcga | 1200 |
| gataatcctg | aagctaaaga | tcctgctgcg | ccatcgcctc | taaatattga | tatggttttg | 1260 |
| gttcaagacc | cgacaacaaa | gagaatcttc | tcaatttatg | atatgttccc | agaaggtcga | 1320 |
| gcagtttttg | gaatgccaaa | acacctgaa | aaagcttatg | aaaagatagg | ggataaaact | 1380 |
| tatcaaatct | tgtataaaca | aggagagtct | ggtcattata | ctgttcgtga | aatggagaa | 1440 |
| gtgtataatg | cacaaaatca | aaagacggat | tatcgtgttg | tagtgaatcc | aacagaacct | 1500 |
| ggctatagag | ataaaggaaa | tctttacaaa | ggtcaggaat | tgattggaaa | tatctatttt | 1560 |
| gcacacagta | caaaaaatcc | atttagagta | gccaatacga | gctatctatg | gatgtcatat | 1620 |
| agtgacgatg | atggtaaaac | ttggtctgca | ccgagagaca | ttactccagg | tcttcgcaag | 1680 |
| gattggatga | agttcctagg | aacaggtcct | ggaacaggaa | ttgtacttcg | gaatgggcct | 1740 |
| cacaagggac | ggattttgat | accggtttat | acgactaata | atgtatctca | cttaaatggc | 1800 |
| tcgcaatctt | ctcgtgtcat | ctattcagat | gatcatggaa | aaacttggca | tgctggagaa | 1860 |
| gcggtcaacg | ataaccgtca | ggtagacggt | caaaagatcc | actcttctac | gatgaacaat | 1920 |
| gaacgtgcgc | aaaatacaga | atcaacggtg | gtacaactaa | acaatggaga | tgttaaactc | 1980 |
| tttatgcgtg | gtttgactgg | agatcttcag | gttgctacaa | gtaaagacgg | aggagtgact | 2040 |
| tgggagaagg | atatcaaacg | ttatccacag | gttaaagatg | tctatgttca | aatgtctgct | 2100 |

-continued

```
atccatacga tgcacgaagg aaaagaatac atcatcctca gtaatgcagg tggaccgaaa      2160
cgtgaaaatg ggatggtcca cttggcacgt gtcgaagaaa atggtgagtt gacttggctc      2220
aaacacaatc caattcaaaa aggagagttt gcctataatt cgctccaaga attaggaaat      2280
ggggagtatg gtatcttgta tgaacatact gaaaaaggac aaaatgccta tacccctatca     2340 tttagaaaat ttaattggga cttttttgagc aaagatctga tttctcctac cgaagcgaaa    2400
gtgaagcgaa ctagagagat gggcaaagga gagatgggca aaggagttat tggcttggag      2460
ttcgactcag aagtattggt caacaaggct ccaaccctttc aattggcaaa tggtaaaaca    2520
gcgactttcc taacccagta tgatagcaag accttgttgt ttgcagtaga taaggaagat      2580
atcggacagg aaattattgg tatagctaaa ggaagcatcg aaagtatgca taatcttcct      2640
gtaaatctag caggtgccag agttcctggc ggagtaaatg gtagcaaagc agcggtgcat      2700
gaagttccag aatttacagg gggagttaat ggtacagagc cagctgttca tgaaatcgca      2760
gagtataagg gatctgattc gcttgtaact cttactacaa aagaagatta tacttacaaa      2820
gctcctcttg ctcagcaggc acttcctgaa acaggaaaca aggagagtga cctcctagct      2880
tcactaggac taacagcttt cttccttggt ctgtttacgc tagggaaaaa gagagaacaa      2940
taa                                                                  2943
```

<210> SEQ ID NO 2
<211> LENGTH: 2094
<212> TYPE: DNA
<213> ORGANISM: Streptococcus pneumoniae strain CGSP14

<400> SEQUENCE: 2

```
atgaataaaa gaggtcttta ttcaaaacta ggaatttctg ttgtaggcat tagtcttta        60 atgggagttc ccactttgat tcatgcgaat gaattaaact atggtcaact gtccatatct      120
cctatttttc aaggaggttc atatcaactg aacaataaga gtatagatat cagctctttg      180
ttattagata aattgtctgg agagagtcag acagtagtaa tgaaatttaa agcagataaa      240
ccaaactctc ttcaagcttt gtttggccta tctaatagta aagcaggctt taaaaataat      300
tacttttcaa tttttcatgag agattctggt gagatagggtg tagaaataag agacgcccaa    360
aagggaataa attatttatt ttctagacca gcttcattat ggggaaagca taaaggacag      420
gcagttgaaa atacactagt atttgtatct gattctaaag ataaaacata cacaatgtat      480
gttaatggaa tagaagtgtt ctctgaaaca gttgatacat ttttgccaat ttcaaatata      540
aatggtatag ataaggcaac actaggagct gttaatcgtg aaggcaagga acattacctc      600
gcaaaaggaa gtattgatga atcagtctta tttaacaaag caattagtga tcaggaagtt      660
tcaaatattc ccttgtcaaa tccatttcag ttaatttttcc aatcaggaga ttctactcaa      720
gctaactatt ttagaatacc gacactatat acattaagta gtggaagagt tctatcaagt      780
attgatgcac gttatggtgg gactcatgat tctaaaagta agattaatat tgccacttct      840
tatagtgatg ataatgggaa aacgtggagt gagccaattt ttgctatgaa gtttaatgac      900
tatgaggagc agttagttta ctggccacga gataaatata taagaatag tcaaattagt      960 ggaagtgctt cattcataga ttcatccatt gttgaagata aaaaatctgg gaaaacgata    1020
ttactagctg atgttatgcc tgcgggtatt ggaaataata atgcaaataa agccgactca    1080
ggttttaaag aaataaatgg tcattattat ttaaaactaa agaagaatgg agataacgat    1140
ttccgttata cagttagaga aaatggtgtc gtttatgatg aaacaactaa taaacctaca    1200
```

| | |
|---|---:|
| aattatacta taaatgataa gtatgaagtt ttggagggag gaaagtctttt aacagtcgaa | 1260 |
| caatattcgg ttgattttga tagtggctct ttaagagaaa aacataatgg aaaacaggtc | 1320 |
| cctatgaatg ttttctacaa agattcgtta tttaaagtga ctcctactaa ttatatagca | 1380 |
| atgacaacta gtcagaatag aggagagagt tgggaacaat ttaagttgtt gcctccgttc | 1440 |
| ttaggagaaa aacataatgg aacttactta tgtcccggac aaggtttagc attaaaatca | 1500 |
| agtaacagat tgattttttgc aacatatact agtggagaac taacctatct catttctgat | 1560 |
| gatagtggtc aaacatggaa gaaatcctca gcttcaattc cgtttaaaaa tgcaacagca | 1620 |
| gaagcacaaa tggttgaact gagagatggt gtgattagaa cattctttag aaccactaca | 1680 |
| ggtaagatag cttatatgac tagtagagat tctggagaaa catggtcgga agtttcgtat | 1740 |
| attgatggaa tccaacaaac ttcatatggc acacaagtat ctgcaattaa atactctcaa | 1800 |
| ttaattgatg gaaaagaagc agtcattttg agtacaccaa attctagaag tggccgtaag | 1860 |
| ggaggtcaat tagttgtcgg tttagtcaat aaagaagatg atagtattga ttggaaatac | 1920 |
| cactatgata ttgatttgcc ttcgtatggt tatgcctatt ctgcgattac agaattgcca | 1980 |
| aatcatcaca taggtgtact gtttgaaaaa tatgattcgt ggtcgagaaa tgaattgcat | 2040 |
| ttaagcaatg tagttcagta tatagatttg gaaattaatg atttaacaaa ataa | 2094 |

<210> SEQ ID NO 3
<211> LENGTH: 2223
<212> TYPE: DNA
<213> ORGANISM: Streptococcus pneumoniae strain CGSP14

<400> SEQUENCE: 3

| | |
|---|---:|
| atgaaaaaaa atattaaaca atacgtaacc ttaggtactg cagtggtatt atcagcattt | 60 |
| gttgctaact cagttgcagc tcaggagact gaaacttctg aagtatcaac accagagttg | 120 |
| gtgcaacctg ttgcaccaac gactccgatt tcggaagtac aacctaaatc gggtaactct | 180 |
| tcggaagtta ctgtacaacc tagaacagtc gaaactactg ttaaggatcc atcttctgca | 240 |
| acggaagaaa ctcctgtctt agaaaaaaat aatgttactt taacagggggg cggagaaaat | 300 |
| gttactaatg agttaaagga taaatttact agcggtgact ttactgtagt gattaagtac | 360 |
| aatcagtcta gtgagaaagg cttacaagct ctgtttggaa tatctaattc taaacccggt | 420 |
| caacaaaata gttatgtaga tgtgttcctt agagacaatg tgaattggga atgaaagcg | 480 |
| cgtgatactt cttccaataa aaatcaccta gtatccagac ctgcttcagt ttggggtaag | 540 |
| tacaaacaag aagctgtgac taacactgtt gcagtagtag cagattcagt caaaaaaaca | 600 |
| tattctttat atgcaaatgg tacaaaagta gtagaaaaga agtggataa cttcttaaac | 660 |
| atcaaggata ttaaaggtat tgattactat atgcttgggg gagtgaaacg tgcaggaaaa | 720 |
| acggcgtttg gttttaacgg aacactagaa aatatcaaat tctttaatag tgcattggat | 780 |
| gaagaaactg ttaaaaagat gacaacaaac gctgttactg acatttaat ttatacggct | 840 |
| aatgatacaa caggttctaa ctatttccgt attccagttc tgtatacttt tagcaatggt | 900 |
| cgggtatttt caagcattga cgctcgttac ggcggaactc atgatttttt gaataaaatt | 960 |
| aatattgcta caagttatag tgatgataat ggtaagacat ggactaaacc aaaattaaca | 1020 |
| ttggcattcg atgattttgc gccagtacca ttagaatggc cttgtgatgt tggtggacgt | 1080 |
| gacttacaaa tcagcggtgg tgcaacctat attgactctg ttattgttga aaaaaataac | 1140 |
| aaacaagtac tcatgtttgc ggatgtgatg cctgctggag taagttttag agaagctact | 1200 |
| agaaaagatt caggttataa acaaattgat ggtaattatt accttaaatt aaagaaacaa | 1260 |

```
ggtgatactg attacaatta tactattcgt gagaatggta ctgtatacga cgatcgtacc    1320
aacagaccaa ctgaattttc agtagataaa aatttcggta ttaaacaaaa tggtaattat    1380
ttgacagtag agcaatattc ggtttcattt aaaaataata aaaagactga atatcgtaat    1440
gggactcacg tccatatgaa tatcttctac aaagatgcat tgttcaaagt agtgccaacg    1500
aactatattg catatatttc tagcaatgat catggcgaat cttggtctgc accaacttta    1560
ttacctccta taatgggact taatcggaat gcgccttatt tgggtcctgg acgtggaatc    1620
attgaaagct caactggacg tattcttatt ccgtcttaca ctggtaaaga gtctgcattc    1680
atttatagtg acgataatgg agcatcttgg aaagttaaag ttgtgccact tccttctagt    1740
tggtcagcag aagcacaatt tgtagaattg agtccaggag taattcaagc atacatgcgt    1800
acaaataatg gtaaaattgc atatttaaca agtacagacg caggtactac ttggagtgca    1860
ccggaatatt tgaaatttgt ttcaaatcca agttatggaa cacaattatc aatcatcaat    1920
tatagtcaac tgattgatgg taaaaaggct gtcattttaa gtactccaaa ctccacaaat    1980
ggtcgtaaac acggacaaat ttggattggt ctaattaatg atgataatac aattgattgg    2040
cgttatcatc acgacgttga ttatagtaac tatggatact catattcaac attgacagag    2100
ttaccaaatc atgaaattgg attgatgttt gaaaaatttg attcatggtc tcgtaatgaa    2160
cttcatatga aaaatgttgt accatatata acatttaaga ttgaagatct gaaaagaat     2220 taa                                                                  2223
```

<210> SEQ ID NO 4
<211> LENGTH: 8241
<212> TYPE: DNA
<213> ORGANISM: Artificial clone
<220> FEATURE:
<223> OTHER INFORMATION: neuraminidase A (NanA), a sialidase A
      precursor, of Streptococcus pneumoniae strain CGSP14 with NCBI
      accession number NC_010582; Locus_Tag= SPCG_1665; protein ID=
      YP 001836382.1. This gene can be amplified by a primer set that
      are NanA-ATG-Kpn1 and

<400> SEQUENCE: 4

```
ggtaccatgt cttatttcag aaatcgggat atagatatag agaggatcag tatgaatcgg     60
agtgttcaag aacgtaagtg tcgttatagc attaggaaac tatcggtagg agcggtttct    120
atgattgtag gagcagtggt atttggaacg tctcctgttt tagctcaaga aggggcaagt    180
gagcaacctc tggcaaatga aactcaactt tcggggggaga gctcaaccct aactgataca    240
gaaaagagcc agccttcttc agagactgaa ctttctggca ataagcaaga acaagaaagg    300
aaagataagc aagaagaaaa aattccaaga gattactatg cacgagattt ggaaaatgtc    360
gaaacagtga tagaaaaaga agatgttgaa accaatgctt caaatggtca gagagttgat    420
ttatcaagtg aactagataa actaaagaaa cttgaaaacg caacagttca catggagttt    480
aagccagatg ccaaggcccc agcattctat aatctctttt ctgtgtcaag tgctactaaa    540
aaagatgagt acttcactat ggcagtttac aataatactg ctactctaga ggggcgtggt    600
tcggatgggc aacagtttta cggtaattac aacgatgcac ccttaaaagt taaaccaggt    660
cagtggaatt ctgtgacttt cacagttgaa aaaccgacag caactacc taaaggccga     720 gtgcgcctct acgtaaacgg ggtattatct cgaacaagtc tgaaatctgg caatttcatt    780
aaagatatgc cagatgtaac gcatgtgcaa atcggagcaa ccaagcgtgc caacaatacg    840
gtttggtggt caaatctaca gattcagaat ctcactgtgt ataatcgtgc tttaacacca    900
```

```
gaagaggtac aaaaacgtag tcaacttttt aaacgctcag atttagaaaa aaaactacct    960
gaaggagcgg ttttaacaga gaaaacggac atattcgaaa gcgggcgtaa cggtaaacca   1020
aataaagatg gaatcaagag ttatcgtatt ccagcacttc tcaagacaga taaaggaact   1080
ttgatcgcag gtgcagatga acgccgtctc cattcgagtg actggggtga tatcggtatg   1140
gtcatcagac gtagtgaaga taatggaaag acatgggag  ataaggtggt tatctccaat   1200
cttcgagata atcctgaagc taaagatcct gctgcgccat cgcctctaaa tattgatatg   1260
gttttggttc aagacccgac aacaaagaga atcttctcaa tttatgatat gttcccagaa   1320
ggtcgagcag ttttttggaat gccaaaaaca cctgaaaaag cttatgaaaa gatggggat   1380
aaaacttatc aaatcttgta taaacaagga gagtctggtc attatactgt tcgtgagaat   1440
ggagaagtgt ataatgcaca aaatcaaaag acgattatc  cgttgtagt gaatccaaca   1500
gaacctggct atagagataa aggaaatctt tacaaaggtc aggaattgat tggaaatatc   1560
tattttgcac acagtacaaa aaatccattt agagtagcca atacgagcta tctatggatg   1620
tcatatagtg acgatgatgg taaaacttgg tctgcaccga gagacattac tccaggtctt   1680
cgcaaggatt ggatgaagtt cctaggaaca ggtcctggaa caggaattgt acttcggaat   1740
gggcctcaca agggacggat tttgataccg gtttatacga ctaataatgt atctcactta   1800
aatggctcgc aatcttctcg tgtcatctat tcagatgatc atggaaaaac ttggcatgct   1860
ggagaagcgg tcaacgataa ccgtcaggta gacggtcaaa agatccactc ttctacgatg   1920
aacaatgaac gtgcgcaaaa tacagaatca acggtggtac aactaaacaa tggagatgtt   1980
aaactcttta tgcgtggttt gactggagat cttcaggttg ctacaagtaa agacggagga   2040
gtgacttggg agaaggatat caaacgttat ccacaggtta agatgtcta  tgttcaaatg   2100
tctgctatcc atacgatgca cgaaggaaaa gaatacatca tcctcagtaa tgcaggtgga   2160
ccgaaacgtg aaaatgggat ggtccacttg gcacgtgtcg aagaaaatgg tgagttgact   2220
tggctcaaac acaatccaat tcaaaaagga gagtttgcct ataattcgct ccaagaatta   2280
ggaaatgggg agtatggtat cttgtatgaa catactgaaa aaggacaaaa tgcctatacc   2340
ctatcattta gaaaatttaa ttgggacttt ttgagcaaag atctgatttc tcctaccgaa   2400
gcgaaagtga agcgaactag agagatgggc aaaggagaga tgggcaaagg agttattggc   2460
ttggagttcg actcagaagt attggtcaac aaggctccaa cccttcaatt ggcaaatggt   2520
aaaacagcga ctttcctaac ccagtatgat agcaagacct tgttgtttgc agtagataag   2580
gaagatatcg gacaggaaat tattggtata gctaaaggaa gcatcgaaag tatgcataat   2640
cttcctgtaa atctagcagg tgccagagtt cctggcggag taaatggtag caaagcagcg   2700
gtgcatgaag ttccagaatt tacaggggga gttaatggta cagagccagc tgttcatgaa   2760
atcgcagagt ataagggatc tgattcgctt gtaactctta ctacaaaaga agattatact   2820
tacaaagctc ctcttgctca gcaggcactt cctgaaacag gaaacaagga gagtgacctc   2880
ctagcttcac taggactaac agcttttcttc cttggtctgt ttacgctagg gaaaaagaga   2940
gaacaactcg agcaccacca ccaccaccac tgagatccgg ctgctaacaa agcccgaaag   3000
gaagctgagt tggctgctgc caccgctgag caataactag cataaccccct tggggcctct   3060
aaacgggtct tgaggggttt tttgctgaaa ggaggaacta tatccggatt ggcgaatggg   3120
acgcgccctg tagcggcgca ttaagcgcgg cgggtgtggt ggttacgcgc agcgtgaccg   3180
ctacacttgc cagcgcccta gcgcccgctc ctttcgcttt cttcccttcc tttctcgcca   3240
cgttcgccgg ctttccccgt caagctctaa atcggggggct cccctttaggg ttccgattta   3300
```

```
gtgctttacg gcacctcgac cccaaaaaac ttgattaggg tgatggttca cgtagtgggc   3360
catcgccctg atagacggtt tttcgccctt tgacgttgga gtccacgttc tttaatagtg   3420
gactcttgtt ccaaactgga acaacactca accctatctc ggtctattct tttgatttat   3480
aagggatttt gccgatttcg gcctattggt taaaaaatga gctgatttaa caaaaattta   3540
acgcgaattt taacaaaata ttaacgttta caatttcagg tggcacttt  cggggaaatg   3600 tgcgcggaac ccctatttgt ttatttttct aaatacattc aaatatgtat ccgctcatga   3660
attaattctt agaaaaactc atcgagcatc aaatgaaact gcaatttatt catatcagga   3720
ttatcaatac catattttg aaaaagccgt ttctgtaatg aaggagaaaa ctcaccgagg   3780
cagttccata ggatggcaag atcctggtat cggtctgcga ttccgactcg tccaacatca   3840
atacaaccta ttaatttccc ctcgtcaaaa ataaggttat caagtgagaa atcaccatga   3900
gtgacgactg aatccggtga gaatggcaaa agtttatgca tttctttcca gacttgttca   3960
acaggccagc cattacgctc gtcatcaaaa tcactcgcat caaccaaacc gttattcatt   4020
cgtgattgcg cctgagcgag acgaaatacg cgatcgctgt taaaaggaca attacaaaca   4080
ggaatcgaat gcaaccggcg caggaacact gccagcgcat caacaatatt ttcacctgaa   4140
tcaggatatt cttctaatac ctggaatgct gttttcccgg ggatcgcagt ggtgagtaac   4200
catgcatcat caggagtacg gataaaatgc ttgatggtcg gaagaggcat aaattccgtc   4260
agccagttta gtctgaccat ctcatctgta acatcattgg caacgctacc tttgccatgt   4320
ttcagaaaca actctggcgc atcgggcttc ccatacaatc gatagattgt cgcacctgat   4380
tgcccgacat tatcgcgagc ccatttatac ccatataaat cagcatccat gttggaattt   4440
aatcgcggcc tagagcaaga cgtttcccgt tgaatatggc tcataacacc ccttgtatta   4500
ctgtttatgt aagcagacag ttttattgtt catgaccaaa atcccttaac gtgagttttc   4560
gttccactga gcgtcagacc ccgtagaaaa gatcaaagga tcttcttgag atccttttt    4620 tctgcgcgta atctgctgct tgcaaacaaa aaaaccaccg ctaccagcgg tggtttgttt   4680
gccggatcaa gagctaccaa ctcttttcc  gaaggtaact ggcttcagca gagcgcagat   4740
accaaatact gtccttctag tgtagccgta gttaggccac cacttcaaga actctgtagc   4800
accgcctaca tacctcgctc tgctaatcct gttaccagtg gctgctgcca gtggcgataa   4860
gtcgtgtctt accgggttgg actcaagacg atagttaccg gataaggcgc agcggtcggg   4920
ctgaacgggg ggttcgtgca cacagcccag cttggagcga acgacctaca ccgaactgag   4980
atacctacag cgtgagctat gagaaagcgc cacgcttccc gaagggagaa aggcggacag   5040
gtatccggta agcggcaggg tcggaacagg agagcgcacg agggagcttc caggggggaa   5100
cgcctggtat ctttatagtc ctgtcgggtt tcgccacctc tgacttgagc gtcgattttt   5160
gtgatgctcg tcaggggggc ggagcctatg gaaaaacgcc agcaacgcgg cctttttacg   5220
gttcctggcc ttttgctggc cttttgctca catgttcttt cctgcgttat cccctgattc   5280
tgtggataac cgtattaccg cctttgagtg agctgatacc gctcgccgca gccgaacgac   5340
cgagcgcagc gagtcagtga gcgaggaagc ggaagagcgc ctgatgcggt attttctcct   5400
tacgcatctg tgcggtattt cacaccgcat atatggtgca ctctcagtac aatctgctct   5460
gatgccgcat agttaagcca gtatacactc cgctatcgct acgtgactgg gtcatggctg   5520
cgccccgaca cccgccaaca cccgctgacg cgccctgacg ggcttgtctg ctcccggcat   5580
ccgcttacag acaagctgtg accgtctccg ggagctgcat gtgtcagagg ttttcaccgt   5640
```

```
catcaccgaa acgcgcgagg cagctgcggt aaagctcatc agcgtggtcg tgaagcgatt      5700
cacagatgtc tgcctgttca tccgcgtcca gctcgttgag tttctccaga agcgttaatg      5760
tctggcttct gataaagcgg gccatgttaa gggcggtttt ttcctgtttg gtcactgatg      5820
cctccgtgta agggggattt ctgttcatgg ggtaatgat accgatgaaa cgagagagga      5880
tgctcacgat acgggttact gatgatgaac atgcccggtt actggaacgt tgtgagggta      5940
aacaactggc ggtatggatg cggcgggacc agagaaaaat cactcagggt caatgccagc      6000
gcttcgttaa tacagatgta ggtgttccac agggtagcca gcagcatcct gcgatgcaga      6060
tccggaacat aatggtgcag ggcgctgact tccgcgtttc cagactttac gaaacacgga      6120
aaccgaagac cattcatgtt gttgctcagg tcgcagacgt tttgcagcag cagtcgcttc      6180
acgttcgctc gcgtatcggt gattcattct gctaaccagt aaggcaaccc cgccagccta      6240
gccgggtcct caacgacagg agcacgatca tgcgcacccg tggggccgcc atgccggcga      6300
taatggcctg cttctcgccg aaacgtttgg tggcgggacc agtgacgaag gcttgagcga      6360
gggcgtgcaa gattccgaat accgcaagcg acaggccgat catcgtcgcg ctccagcgaa      6420
agcggtcctc gccgaaaatg acccagagcg ctgccggcac ctgtcctacg agttgcatga      6480
taaagaagac agtcataagt gcggcgacga tagtcatgcc ccgcgcccac cggaaggagc      6540
tgactgggtt gaaggctctc aagggcatcg gtcgagatcc cggtgcctaa tgagtgagct      6600
aacttacatt aattgcgttg cgctcactgc ccgctttcca gtcgggaaac ctgtcgtgcc      6660
agctgcatta atgaatcggc caacgcgcgg ggagaggcgg tttgcgtatt gggcgccagg      6720
gtggtttttc ttttcaccag tgagacgggc aacagctgat tgcccttcac cgcctggccc      6780
tgagagagtt gcagcaagcg gtccacgctg gtttgcccca gcaggcgaaa atcctgtttg      6840
atggtggtta acggcgggat ataacatgag ctgtcttcgg tatcgtcgta tcccactacc      6900
gagatgtccg caccaacgcg cagcccggac tcggtaatgg cgcgcattgc gcccagcgcc      6960
atctgatcgt tggcaaccag catccgcagtg gaacgatgc cctcattcag catttgcatg      7020
gtttgttgaa accggacat ggcactccag tcgccttccc gttccgctat cggctgaatt      7080
tgattgcgag tgagatattt atgccagcca gcagacgca gacgcgccga gacagaactt      7140
aatgggcccg ctaacagcgc gatttgctgg tgacccaatg cgaccagatg ctccacgccc      7200
agtcgcgtac cgtcttcatg ggagaaaata atactgttga tgggtgtctg gtcagagaca      7260
tcaagaaata cgccggaac attagtgcag gcagcttcca cagcaatggc atcctggtca      7320
tccagcggat agttaatgat cagcccactg acgcgttgcg cgagaagatt gtgcaccgcc      7380
gctttacagg cttcgacgcc gcttcgttct accatcgaca ccaccacgct ggcacccagt      7440
tgatcggcgc gagatttaat cgccgcgaca atttgcgacg gcgcgtgcag gccagactg      7500 gaggtggcaa cgccaatcag caacgactgt ttgcccgcca gttgttgtgc cacgcggttg      7560
ggaatgtaat tcagctccgc catcgccgct tccactttt cccgcgtttt cgcagaaacg      7620
tggctggcct ggttcaccac gcgggaaacg gtctgataag agacaccggc atactctgcg      7680
acatcgtata acgttactgg tttcacattc accaccctga attgactctc ttccgggcgc      7740
tatcatgcca taccgcgaaa ggttttgcgc cattcgatgg tgtccgggat ctcgacgctc      7800
tcccttatgc gactcctgca ttaggaagca gcccagtagt aggttgaggc cgttgagcac      7860
cgccgccgca aggaatggtg catgcaagga tggcgcccc aacagtcccc ggccacggg      7920 gcctgccacc atacccacgc cgaaacaagc gctcatgagc ccgaagtggc gagcccgatc      7980
ttccccatcg gtgatgtcgg cgatataggc gccagcaacc gcacctgtgg cgccggtgat      8040
```

```
gccggccacg atgcgtccgg cgtagaggat cgagatcgat ctcgatcccg cgaaattaat    8100
acgactcact atagggggaat tgtgagcgga taacaattcc cctctagaaa taattttgtt    8160
taactttaag aaggagatat acatatgaaa gaaaccgctg ctgctaaatt cgaacgccag    8220
cacatggaca gcccagatct g                                              8241
```

<210> SEQ ID NO 5
<211> LENGTH: 7392
<212> TYPE: DNA
<213> ORGANISM: Artificial clone

<400> SEQUENCE: 5

```
ggtaccatga ataaaagagg tctttattca aaactaggaa tttctgttgt aggcattagt      60
cttttaatgg gagttccccac tttgattcat gcgaatgaat taaactatgg tcaactgtcc    120
atatctccta ttttttcaagg aggttcatat caactgaaca ataagagtat agatatcagc    180
tctttgttat tagataaatt gtctggagag agtcagacag tagtaatgaa atttaaagca    240
gataaaccaa actctcttca agctttgttt ggcctatcta atagtaaagc aggctttaaa    300
aataattact tttcaatttt catgagagat tctggtgaga taggtgtaga aataagagac    360
gcccaaaagg gaataaatta tttatttcct agaccagctt cattatgggg aaagcataaa    420
ggacaggcag ttgaaaatac actagtattt gtatctgatt ctaaagataa aacatacaca    480
atgtatgtta atggaataga agtgttctct gaaacagttg atacatttt gccaatttca    540 aatataaatg gtatagataa ggcaacacta ggagctgtta atcgtgaagg caaggaacat    600
tacctcgcaa aaggaagtat tgatgaaatc agtctattta caaagcaat tagtgatcag    660 gaagtttcaa atattcccctt gtcaaatcca tttcagttaa ttttccaatc aggagattct    720
actcaagcta actattttag aataccgaca ctatatacat taagtagtgg aagagttcta    780
tcaagtattg atgcacgtta tggtgggact catgattcta aaagtaagat taatattgcc    840
acttcttata gtgatgataa tgggaaaacg tggagtgagc caatttttgc tatgaagttt    900
aatgactatg aggagcagtt agtttactgg ccacgagata taaaattaaa gaatagtcaa    960
attagtggaa gtgcttcatt catagattca tccattgttg aagataaaaa atctgggaaa   1020
acgatattac tagctgatgt tatgcctgcg ggtattggaa ataataatgc aaataaagcc   1080
gactcaggtt ttaagaaaat aaatggtcat tattatttaa aactaaagaa gaatggagat   1140
aacgatttcc gttatacagt tagagaaaat ggtgtcgttt atgatgaaac aactaataaa   1200
cctacaaatt atactataaa tgataagtat gaagttttgg agggaggaaa gtctttaaca   1260
gtcgaacaat attcggttga ttttgatagt ggctctttaa gagaaaaaca taatggaaaa   1320
caggtcccta tgaatgtttt ctacaaagat tcgttattta aagtgactcc tactaattat   1380
atagcaatga caactagtca gaatagagga gagagttggg aacaatttaa gttgttgcct   1440
ccgttcttag gagaaaaaca taatggaact tactatgtc ccggacaagg tttagcatta   1500
aaatcaagta acagattgat ttttgcaaca tatactagtg gagaactaac ctatctcatt   1560
tctgatgata gtggtcaaac atggaagaaa tcctcagctt caattccgtt taaaaatgca   1620
acagcagaag cacaaatggt tgaactgaga gatggtgtga ttagaacatt ctttagaacc   1680
actacaggta agatagctta tgactagt agagattctg gagaaacatg gtcggaagtt   1740
tcgtatattg atggaatcca acaaacttca tatggcacac aagtatctgc aattaaatac   1800
tctcaattaa ttgatggaaa agaagcagtc attttgagta caccaaattc tagaagtggc   1860
```

```
cgtaagggag gtcaattagt tgtcggttta gtcaataaag aagatgatag tattgattgg    1920
aaataccact atgatattga tttgccttcg tatggttatg cctattctgc gattacagaa    1980
ttgccaaatc atcacatagg tgtactgttt gaaaaatatg attcgtggtc gagaaatgaa    2040
ttgcatttaa gcaatgtagt tcagtatata gatttggaaa ttaatgattt aacaaaactc    2100
gagcaccacc accaccacca ctgagatccg gctgctaaca aagcccgaaa ggaagctgag    2160
ttggctgctg ccaccgctga gcaataacta gcataacccc ttggggcctc taaacgggtc    2220
ttgaggggtt ttttgctgaa aggaggaact atatccggat tggcgaatgg gacgcgccct    2280
gtagcggcgc attaagcgcg gcgggtgtgg tggttacgcg cagcgtgacc gctacacttg    2340
ccagcgccct agcgcccgct cctttcgctt tcttcccttc ctttctcgcc acgttcgccg    2400
gctttccccg tcaagctcta aatcgggggc tccctttagg gttccgattt agtgctttac    2460
ggcacctcga ccccaaaaaa cttgattagg gtgatggttc acgtagtggg ccatcgccct    2520
gatagacggt ttttcgccct ttgacgttgg agtccacgtt ctttaatagt ggactcttgt    2580
tccaaactgg aacaacactc aaccctatct cggtctattc ttttgattta agggattt     2640 tgccgatttc ggcctattgg ttaaaaaatg agctgattta acaaaatttt aacgcgaatt    2700
ttaacaaaat attaacgttt acaatttcag gtggcacttt tcggggaaat gtgcgcggaa    2760
cccctatttg tttatttttc taaatacatt caaatatgta tccgctcatg aattaattct    2820
tagaaaaact catcgagcat caaatgaaac tgcaatttat tcatatcagg attatcaata    2880
ccatattttt gaaaaagccg tttctgtaat gaaggagaaa actcaccgag gcagttccat    2940 aggatgcaa gatcctggta tcggtctgcg attccgactc gtccaacatc aatacaacct    3000
attaatttcc cctcgtcaaa aataaggtta tcaagtgaga atcaccatg agtgacgact    3060 gaatccggtg agaatggcaa aagtttatgc atttctttcc agacttgttc aacaggccag    3120
ccattacgct cgtcatcaaa atcactcgca tcaaccaaac cgttattcat tcgtgattgc    3180
gcctgagcga gacgaaatac gcgatcgctg ttaaaaggac aattacaaac aggaatcgaa    3240
tgcaaccggc gcaggaacac tgccagcgca tcaacaatat tttcacctga atcaggatat    3300
tcttctaata cctggaatgc tgttttcccg gggatcgcag tggtgagtaa ccatgcatca    3360
tcaggagtac ggataaaatg cttgatggtc ggaagaggca taaattccgt cagccagttt    3420
agtctgacca tctcatctgt aacatcattg gcaacgctac ctttgccatg tttcagaaac    3480
aactctggcg catcgggctt cccatacaat cgatagattg tcgcacctga ttgcccgaca    3540
ttatcgcgag cccatttata cccatataaa tcagcatcca tgttggaatt taatcgcggc    3600
ctagagcaag acgtttcccg ttgaatatgg ctcataacac cccttgtatt actgtttatg    3660
taagcagaca gttttattgt tcatgaccaa atcccttaa cgtgagtttt cgttccactg    3720
agcgtcagac cccgtagaaa agatcaaagg atcttcttga gatcctttt ttctgcgcgt    3780 aatctgctgc ttgcaaacaa aaaaaccacc gctaccagcg gtggtttgtt tgccggatca    3840
agagctacca actctttttc cgaaggtaac tggcttcagc agagcgcaga taccaaatac    3900
tgtccttcta gtgtagccgt agttaggcca ccacttcaag aactctgtag caccgcctac    3960
atacctcgct ctgctaatcc tgttaccagt ggctgctgcc agtggcgata agtcgtgtct    4020
taccgggttg gactcaagac gatagttacc ggataaggcg cagcggtcgg gctgaacggg    4080
gggttcgtgc acacagccca gcttggagcg aacgacctac accgaactga gatacctaca    4140
gcgtgagcta tgagaaagcg ccacgcttcc cgaagggaga aaggcggaca ggtatccggt    4200
aagcggcagg gtcggaacag gagagcgcac gagggagctt ccagggggaa acgcctggta    4260
```

```
tctttatagt cctgtcgggt ttcgccacct ctgacttgag cgtcgatttt tgtgatgctc    4320
gtcagggggg cggagcctat ggaaaaacgc cagcaacgcg gccttttac ggttcctggc     4380 cttttgctgg ccttttgctc acatgttctt tcctgcgtta tccctgatt ctgtggataa     4440 ccgtattacc gcctttgagt gagctgatac cgctcgccgc agccgaacga ccgagcgcag    4500
cgagtcagtg agcgaggaag cggaagagcg cctgatgcgg tattttctcc ttacgcatct    4560
gtgcggtatt tcacaccgca tatatggtgc actctcagta caatctgctc tgatgccgca    4620
tagttaagcc agtatacact ccgctatcgc tacgtgactg ggtcatggct gcgccccgac    4680
acccgccaac acccgctgac gcgccctgac gggcttgtct gctcccggca tccgcttaca    4740
gacaagctgt gaccgtctcc gggagctgca tgtgtcagag gttttcaccg tcatcaccga    4800
aacgcgcgag gcagctgcgg taaagctcat cagcgtggtc gtgaagcgat tcacagatgt    4860
ctgcctgttc atccgcgtcc agctcgttga gtttctccag aagcgttaat gtctggcttc    4920
tgataaagcg ggccatgtta agggcggttt tttcctgttt ggtcactgat gcctccgtgt    4980 aaggggatt tctgttcatg ggggtaatga taccgatgaa acgagagagg atgctcacga    5040
tacgggttac tgatgatgaa catgcccggt tactggaacg ttgtgagggt aaacaactgg    5100
cggtatggat gcggcgggac cagagaaaaa tcactcaggg tcaatgccag cgcttcgtta    5160
atacagatgt aggtgttcca cagggtagcc agcagcatcc tgcgatgcag atccggaaca    5220
taatggtgca gggcgctgac ttccgcgttt ccagacttta cgaaacacgg aaaccgaaga    5280
ccattcatgt tgttgctcag gtcgcagacg ttttgcagca gcagtcgctt cacgttcgct    5340
cgcgtatcgg tgattcattc tgctaaccag taaggcaacc ccgccagcct agccgggtcc    5400
tcaacgacag gagcacgatc atgcgcaccc gtggggccgc catgccggcg ataatggcct    5460
gcttctcgcc gaaacgtttg gtggcgggac cagtgacgaa ggcttgagcg agggcgtgca    5520
agattccgaa taccgcaagc gacaggccga tcatcgtcgc gctccagcga aagcggtcct    5580
cgccgaaaat gacccagagc gctgccggca cctgtcctac gagttgcatg ataaagaaga    5640
cagtcataag tgcggcgacg atagtcatgc cccgcgccca ccggaaggag ctgactgggt    5700
tgaaggctct caagggcatc ggtcgagatc ccggtgccta atgagtgagc taacttacat    5760
taattgcgtt gcgctcactg cccgctttcc agtcgggaaa cctgtcgtgc cagctgcatt    5820
aatgaatcgg ccaacgcgcg gggagaggcg gtttgcgtat tgggcgccag ggtggttttt    5880
cttttcacca gtgagacggg caacagctga ttgcccttca ccgcctggcc ctgagagagt    5940
tgcagcaagc ggtccacgct ggtttgcccc agcaggcgaa atcctgtttt gatggtggtt    6000
aacggcggga tataacatga gctgtcttcg gtatcgtcgt atcccactac cgagatgtcc    6060
gcaccaacgc gcagcccgga ctcggtaatg gcgcgcattg cgcccagcgc catctgatcg    6120
ttggcaacca gcatcgcagt gggaacgatg ccctcattca gcatttgcat ggtttgttga    6180
aaaccggaca tggcactcca gtcgccttcc cgttccgcta tcggctgaat ttgattgcga    6240
gtgagatatt tatgccagcc agccagacgc agacgcgccg agacagaact taatgggccc    6300
gctaacagcg cgatttgctg gtgacccaat gcgaccagat gctccacgcc cagtcgcgta    6360
ccgtcttcat gggagaaaat aatactgttg atgggtgtct ggtcagagac atcaagaaat    6420
aacgccggaa cattagtgca ggcagcttcc acagcaatgg catcctggtc atccagcgga    6480
tagttaatga tcagcccact gacgcgttgc gcgagaagat tgtgcaccgc cgctttacag    6540
gcttcgacgc cgcttcgttc taccatcgac accaccacgc tggcacccag ttgatcggcg    6600
```

```
cgagatttaa tcgccgcgac aatttgcgac ggcgcgtgca gggccagact ggaggtggca    6660
acgccaatca gcaacgactg tttgcccgcc agttgttgtg ccacgcggtt gggaatgtaa    6720
ttcagctccg ccatcgccgc ttccactttt tcccgcgttt tcgcagaaac gtggctggcc    6780
tggttcacca cgcggggaaac ggtctgataa gagacaccgg catactctgc gacatcgtat    6840
aacgttactg gtttcacatt caccaccctg aattgactct cttccgggcg ctatcatgcc    6900
ataccgcgaa aggttttgcg ccattcgatg gtgtccggga tctcgacgct ctcccttatg    6960
cgactcctgc attaggaagc agcccagtag taggttgagg ccgttgagca ccgccgccgc    7020
aaggaatggt gcatgcaagg agatggcgcc caacagtccc ccggccacgg ggcctgccac    7080
catacccacg ccgaaacaag cgctcatgag cccgaagtgg cgagcccgat cttccccatc    7140
ggtgatgtcg gcgatatagg cgccagcaac cgcacctgtg gcgccggtga tgccggccac    7200
gatgcgtccg gcgtagagga tcgagatcga tctcgatccc gcgaaattaa tacgactcac    7260
tatagggaa ttgtgagcgg ataacaattc ccctctagaa ataattttgt ttaactttaa    7320
gaaggagata tacatatgaa agaaaccgct gctgctaaat tcgaacgcca gcacatggac    7380
agcccagatc tg                                                        7392
```

<210> SEQ ID NO 6
<211> LENGTH: 7521
<212> TYPE: DNA
<213> ORGANISM: Artificial clone

<400> SEQUENCE: 6

```
ggtaccatga aaaaaatat taaacaatac gtaaccttag gtactgcagt ggtattatca      60
gcatttgttg ctaactcagt tgcagctcag gagactgaaa cttctgaagt atcaacacca     120
gagttggtgc aacctgttgc accaacgact ccgatttcgg aagtacaacc taaatcgggt    180
aactcttcgg aagttactgt acaacctaga acagtcgaaa ctactgttaa ggatccatct    240
tctgcaacgg aagaaactcc tgtcttagaa aaaataatg ttactttaac aggggcgga    300
gaaaatgtta ctaatgagtt aaaggataaa tttactagcg gtgactttac tgtagtgatt   360
aagtacaatc agtctagtga gaaaggctta caagctctgt ttggaatatc taattctaaa   420
cccggtcaac aaaatagtta tgtagatgtg ttccttagag acaatggtga attgggaatg    480
gaagcgcgtg atacttcttc caataaaaat cacctagtat ccagacctgc ttcagtttgg    540
ggtaagtaca acaagaagc tgtgactaac actgttgcag tagtagcaga ttcagtcaaa    600
aaaacatatt ctttatatgc aaatggtaca aagtagtag aaaagaaagt ggataacttc    660
ttaaacatca aggatattaa aggtattgat tactatatgc ttgggggagt gaaacgtgca    720
ggaaaaacgg cgtttggttt taacggaaca ctagaaaata tcaaattctt taatagtgca    780
ttggatgaag aaactgttaa aaagatgaca acaaacgctg ttactggaca tttaatttat    840
acggctaatg atacaacagg ttctaactat ttccgtattc cagttctgta acttttagc    900
aatggtcggg tattttcaag cattgacgct cgttacggcg gaactcatga ttttttgaat   960
aaaattaata ttgctacaag ttatagtgat gataatggta agacatggac taaaccaaaa   1020
ttaacattgg cattcgatga ttttgcgcca gtaccattag aatggccttg tgatgttggt   1080
ggacgtgact tacaaatcag cggtggtgca acctatattg actctgttat tgttgaaaaa    1140
ataacaaac aagtactcat gtttgcggat gtgatgcctg ctggagtaag ttttagagaa     1200
gctactagaa aagattcagg ttataaacaa attgatggta attattacct taaattaaag    1260
aaacaaggtg atactgatta caattatact attcgtgaga atggtactgt atacgacgat    1320
```

```
cgtaccaaca gaccaactga attttcagta gataaaaatt tcggtattaa acaaaatggt    1380
aattatttga cagtagagca atattcggtt tcatttaaaa ataataaaaa gactgaatat    1440
cgtaatggga ctcacgtcca tatgaatatc ttctacaaag atgcattgtt caaagtagtg    1500
ccaacgaact atattgcata tatttctagc aatgatcatg gcgaatcttg gtctgcacca    1560
actttattac ctcctataat gggacttaat cggaatgcgc cttatttggg tcctggacgt    1620
ggaatcattg aaagctcaac tggacgtatt cttattccgt cttacactgg taaagagtct    1680
gcattcattt atagtgacga taatggagca tcttggaaag ttaaagttgt gccacttcct    1740
tctagttggt cagcagaagc acaatttgta gaattgagtc caggagtaat tcaagcatac    1800
atgcgtacaa ataatggtaa aattgcatat ttaacaagta cagacgcagg tactacttgg    1860
agtgcaccgg aatatttgaa atttgtttca aatccaagtt atggaacaca attatcaatc    1920
atcaattata gtcaactgat tgatggtaaa aaggctgtca ttttaagtac tccaaactcc    1980
acaaatggtc gtaaacacgg acaaatttgg attggtctaa ttaatgatga taatacaatt    2040
gattggcgtt atcatcacga cgttgattat agtaactatg gatactcata ttcaacattg    2100
acagagttac caaatcatga aattggattg atgtttgaaa aatttgattc atggtctcgt    2160
aatgaacttc atatgaaaaa tgttgtacca tatataacat ttaagattga agatctgaaa    2220
aagaatctcg agcaccacca ccaccaccac tgagatccgg ctgctaacaa agcccgaaag    2280
gaagctgagt tggctgctgc caccgctgag caataactag cataacccct ggggcctct    2340 aaacgggtct tgaggggttt tttgctgaaa ggaggaacta tatccggatt ggcgaatggg    2400
acgcgccctg tagcggcgca ttaagcgcgg cgggtgtggt ggttacgcgc agcgtgaccg    2460
ctacacttgc cagcgcccta gcgcccgctc ctttcgcttt cttcccttcc tttctcgcca    2520
cgttcgccgg ctttccccgt caagctctaa atcgggggct ccctttaggg ttccgattta    2580
gtgctttacg gcacctcgac cccaaaaaac ttgattaggg tgatggttca cgtagtgggc    2640
catcgccctg atagacggtt tttcgccctt tgacgttgga gtccacgttc tttaatagtg    2700
gactcttgtt ccaaactgga acaacactca accctatctc ggtctattct tttgatttat    2760
aagggatttt gccgatttcg gcctattggt taaaaaatga gctgatttaa caaaaattta    2820
acgcgaattt taacaaaata ttaacgttta caatttcagg tggcacttt cggggaaatg    2880 tgcgcggaac ccctatttgt ttatttttct aaatacattc aaatatgtat ccgctcatga    2940
attaattctt agaaaaactc atcgagcatc aaatgaaact gcaatttatt catatcagga    3000
ttatcaatac catattttg aaaaagccgt ttctgtaatg aaggagaaaa ctcaccgagg    3060
cagttccata ggatggcaag atcctggtat cggtctgcga ttccgactcg tccaacatca    3120
atacaaccta ttaatttccc ctcgtcaaaa ataaggttat caagtgagaa atcaccatga    3180
gtgacgactg aatccggtga gaatggcaaa agtttatgca tttctttcca gacttgttca    3240
acaggccagc cattacgctc gtcatcaaaa tcactcgcat caaccaaacc gttattcatt    3300
cgtgattgcg cctgagcgag acgaaatacg cgatcgctgt taaaaggaca attacaaaca    3360
ggaatcgaat gcaaccggcg caggaacact gccagcgcat caacaatatt ttcacctgaa    3420
tcaggatatt cttctaatac ctggaatgct gtttccccgg ggatcgcagt ggtgagtaac    3480
catgcatcat caggagtacg gataaaatgc ttgatggtcg aagaggcat aaattccgtc    3540 agccagttta gtctgaccat ctcatctgta acatcattgg caacgctacc tttgccatgt    3600
ttcagaaaca actctggcgc atcgggcttc ccatacaatc gatagattgt cgcacctgat    3660
```

```
tgcccgacat tatcgcgagc ccatttatac ccatataaat cagcatccat gttggaattt   3720
aatcgcggcc tagagcaaga cgtttcccgt tgaatatggc tcataacacc ccttgtatta   3780
ctgtttatgt aagcagacag ttttattgtt catgaccaaa atcccttaac gtgagttttc   3840
gttccactga gcgtcagacc ccgtagaaaa gatcaaagga tcttcttgag atccttttt   3900 tctgcgcgta atctgctgct tgcaaacaaa aaaaccaccg ctaccagcgg tggtttgttt   3960
gccggatcaa gagctaccaa ctcttttttcc gaaggtaact ggcttcagca gagcgcagat   4020
accaaatact gtccttctag tgtagccgta gttaggccac cacttcaaga actctgtagc   4080
accgcctaca tacctcgctc tgctaatcct gttaccagtg ctgctgcca gtggcgataa   4140 gtcgtgtctt accgggttgg actcaagacg atagttaccg gataaggcgc agcggtcggg   4200
ctgaacgggg ggttcgtgca cacagcccag cttggagcga acgacctaca ccgaactgag   4260
atacctacag cgtgagctat gagaaagcgc cacgcttccc gaagggagaa aggcggacag   4320
gtatccggta agcggcaggg tcggaacagg agagcgcacg agggagcttc caggggggaaa   4380 cgcctggtat ctttatagtc ctgtcgggtt tcgccacctc tgacttgagc gtcgatttt   4440 gtgatgctcg tcaggggggc ggagcctatg gaaaaacgcc agcaacgcgg cctttttacg   4500
gttcctggcc ttttgctggc cttttgctca catgttcttt cctgcgttat cccctgattc   4560
tgtggataac cgtattaccg cctttgagtg agctgatacc gctcgccgca gccgaacgac   4620
cgagcgcagc gagtcagtga gcgaggaagc ggaagagcgc ctgatgcggt attttctcct   4680
tacgcatctg tgcggtattt cacaccgcat atatggtgca ctctcagtac aatctgctct   4740
gatgccgcat agttaagcca gtatacactc cgctatcgct acgtgactgg gtcatggctg   4800
cgccccgaca cccgccaaca cccgctgacg cgccctgacg ggcttgtctg ctcccggcat   4860
ccgcttacag acaagctgtg accgtctccg ggagctgcat gtgtcagagg ttttcaccgt   4920
catcaccgaa acgcgcgagg cagctgcggt aaagctcatc agcgtggtcg tgaagcgatt   4980
cacagatgtc tgcctgttca tccgcgtcca gctcgttgag tttctccaga agcgttaatg   5040
tctggcttct gataaagcgg gccatgttaa gggcggtttt ttcctgtttg gtcactgatg   5100
cctccgtgta aggggattt ctgttcatgg ggtaatgat accgatgaaa cgagagagga   5160
tgctcacgat acgggttact gatgatgaac atgcccggtt actggaacgt tgtgagggta   5220
aacaactggc ggtatggatg cggcgggacc agagaaaaat cactcagggt caatgccagc   5280
gcttcgttaa tacagatgta ggtgttccac agggtagcca gcagcatcct gcgatgcaga   5340
tccggaacat aatggtgcag gcgctgact tccgcgtttc cagactttac gaaacacgga   5400
aaccgaagac cattcatgtt gttgctcagg tcgcagacgt tttgcagcag cagtcgcttc   5460
acgttcgctc gcgtatcggt gattcattct gctaaccagt aaggcaaccc cgccagccta   5520
gccgggtcct caacgacagg agcacgatca tgcgcacccg tggggccgcc atgccggcga   5580
taatggcctg cttctcgccg aaacgtttgg tggcggacc agtgacgaag gcttgagcga   5640
gggcgtgcaa gattccgaat accgcaagcg acaggccgat catcgtcgcg ctccagcgaa   5700
agcggtcctc gccgaaaatg acccagagcg ctgccggcac ctgtcctacg agttgcatga   5760
taaagaagac agtcataagt gcggcgacga tagtcatgcc ccgcgcccac cggaaggagc   5820
tgactgggtt gaaggctctc aagggcatcg gtcgagatcc cggtgcctaa tgagtgagct   5880
aacttacatt aattgcgttg cgctcactgc ccgctttcca gtcgggaaac ctgtcgtgcc   5940
agctgcatta atgaatcggc caacgcgcgg ggagaggcgg tttgcgtatt gggcgccagg   6000
gtggtttttc ttttcaccag tgagacgggc aacagctgat tgcccttcac cgcctggccc   6060
```

```
tgagagagtt gcagcaagcg gtccacgctg gtttgcccca gcaggcgaaa atcctgtttg    6120
atggtggtta acggcgggat ataacatgag ctgtcttcgg tatcgtcgta tcccactacc    6180
gagatgtccg caccaacgcg cagcccggac tcggtaatgg cgcgcattgc gcccagcgcc    6240
atctgatcgt tggcaaccag catcgcagtg ggaacgatgc cctcattcag catttgcatg    6300
gtttgttgaa aaccggacat ggcactccag tcgccttccc gttccgctat cggctgaatt    6360
tgattgcgag tgagatattt atgccagcca gccagacgca gacgcgccga gacagaactt    6420
aatgggcccg ctaacagcgc gatttgctgg tgacccaatg cgaccagatg ctccacgccc    6480
agtcgcgtac cgtcttcatg ggagaaaata atactgttga tgggtgtctg gtcagagaca    6540
tcaagaaata acgccggaac attagtgcag gcagcttcca cagcaatggc atcctggtca    6600
tccagcggat agttaatgat cagcccactg acgcgttgcg cgagaagatt gtgcaccgcc    6660
gctttacagg cttcgacgcc gcttcgttct accatcgaca ccaccacgct ggcacccagt    6720
tgatcggcgc gagatttaat cgccgcgaca atttgcgacg gcgcgtgcag ggccagactg    6780
gaggtggcaa cgccaatcag caacgactgt ttgcccgcca gttgttgtgc cacgcggttg    6840
ggaatgtaat tcagctccgc catcgccgct tccactttt  cccgcgtttt cgcagaaacg    6900
tggctggcct ggttcaccac gcgggaaacg gtctgataag agacaccggc atactctgcg    6960
acatcgtata acgttactgg tttcacattc accaccctga attgactctc ttccgggcgc    7020
tatcatgcca taccgcgaaa ggttttgcgc cattcgatgg tgtccgggat ctcgacgctc    7080
tcccttatgc gactcctgca ttaggaagca gcccagtagt aggttgaggc cgttgagcac    7140
cgccgccgca aggaatggtg catgcaagga gatggcgccc aacagtcccc cggccacggg    7200
gcctgccacc atacccacgc cgaaacaagc gctcatgagc ccgaagtggc gagcccgatc    7260
ttccccatcg gtgatgtcgg cgatataggc gccagcaacc gcacctgtgg cgccggtgat    7320
gccggccacg atgcgtccgg cgtagaggat cgagatcgat ctcgatcccg cgaaattaat    7380
acgactcact atagggaat  tgtgagcgga taacaattcc cctctagaaa taatttgtt   7440 taactttaag aaggagatat acatatgaaa gaaaccgctg ctgctaaatt cgaacgccag    7500
cacatggaca gcccagatct g                                              7521
```

METHOD OF DIAGNOSING AND PREVENTING PNEUMOCOCCAL DISEASES USING PNEUMOCOCCAL NEURAMINIDASES

FIELD OF THE INVENTION

The present invention relates to the development of vaccine for preventing pneumococcal diseases, and to the diagnosis of the pneumococci-infected samples not just from urine but also from blood and pleural effusion in pyothorax. More particularly, this invention relates to a universal protein vaccine against the pneumococcal infection.

BACKGROUND OF THE INVENTION

*Streptococcus pneumoniae* is one of Gram-positive encapsulated diplococci. Pneumococcal infection is a leading infectious cause of the high mortality and morbidity worldwide, especially among young children below two years of age and the elderly over sixty years of age. Globally, pneumococcal infection has been estimated to cause about 1.6 million deaths annually, including 1 million children less than five years old. Even though certain vaccines have been applied to prevent the *S. pneumoniae* infection, the mortality rate caused by this organism is still ranked the highest. The spectrum of the *S. pneumoniae*-related diseases includes invasive pneumococcal disease (IPD), such as sepsis and meningitis; lower respiratory infections, such as bacterial pneumonia; and upper respiratory infections, such as acute otitis media (AOM) (Tuomanen et al., 1995).

According to the reports of World Health Organization (WHO) in 2005, acute respiratory tract infections were the major cause of death globally, in which the deaths were chiefly attributable to the *S. pneumoniae*-associated community-acquired pneumonia (CAP). This threatening issue strongly raises the urgency for both diagnosis and prevention. Although the diagnoses of pneumococci have been developed for decades, we still heavily rely on conventional culture methods that are tedious and time-consuming, to proliferate enough bacteria for specific and sensitive detection. Therefore, based on specific DNA amplification and antigen detection, the tests of non-culture samples from sputum, urine, and blood have been continuously developed over time in order to identify pneumococci as the etiological agent of diseases. However, the consequences of those tests were always unsatisfactory in certain applications. For instance, the application of PCR testing for the diagnosis of IPD has ever shown to be insufficiently sensitive when using blood or urinary samples, and poorly specific when using respiratory samples. To overcome the problem of poor specificity when using sputum samples, recently a dual-PCR testing protocol using pneumococcal lytA and ply as targets has been successfully developed and evaluated.

Another disappointing aspect for diagnosis revealed that only one third of pathogens could be recovered from patient's sputum when using conventional culture methods. In addition, the controversial results lack specificity correlated to CAP because nasopharyngeal carriage of pneumococci could also be found in both healthy individuals and inadequate sputum samples. In addition, the etiological pathogens of CAP tested from blood culture and pleural fluid were specific, but the positive rates were lower (<30%) compared to that from sputum sample. For this reason, the development of antigen detection was applied to compensate the drawback of low specificity. Higher sensitivity of the pleural test compared to pleural cultures indicated that antigen detection for pleural samples rather than pleural culture could be a better application for the CAP study of pneumococcal etiology. Also, the detection of BinaxNOW pneumococcal C-polysaccharide in a urine sample with CAP shows unsatisfied result due to its high rate of false positive.

Currently, there are two kinds of vaccines, 23-valent pneumococcal polysaccharide vaccine (PPV23) and 7-valent pneumococcal conjugate vaccine (PCV7), available for general protection against potential IPD-causative pathogen strains. Vaccine PCV7 can target seven serotypes, including 4, 6B, 9V, 14, 18C, 19F, and 23F. Before the introduction of PCV7, the PCV7-targeted 7 serotypes (4, 6B, 9V, 14, 18C, 19F, and 23F) were responsible for about 90% of incidence of IPD in young children in the United States and for more than 60% of those in Europe. After PCV7 vaccination, the cases of IPD in children less than 5 years old declined by 56% in 2001 and by 76% in 2004. In contrast, PPV23 vaccination seems to difficultly reach firm conclusions in clinical effectiveness (around 50-70% effective). Although two doses of PCV7 and following one dose of PPV23 were recommended to broaden protection, the effectiveness of vaccines was significant on the protection of those seven PCV7-covered serotypes rather than others. The results suggested that PPV23 seems not necessary as a boost dose for broadening protection.

At least 93 different polysaccharide (PS) capsules of *S. pneumoniae* have been verified to be specific serotypes, and further classified to be 46 serogroups. Among all pathogenic pneumoncocci worldwide, serotype 14 and serogroup 6 are predominant. In addition, the majority of IPD is generally caused by about 15 serotypes. However, only a few antimicrobial resistant pneumococcal clones could spread fast. The incidence of antimicrobial resistance of pneumococci varies regionally, and is associated with the spectrum of antibiotic use, population density, the indigenous prevalence of resistant strains, ages and time. Although the resistance patterns have been shown to be different around the world, the predominant serotypes commonly identified are 6A/B, 9V, 14, 19A/F, and 23F. Based on epidemiological study, the nasopharyngeal (NP) carriage of predominant pneumococci has been observed in many young children, indicating that NP carriage may play an important role in pneumococcal transmission, especially for antibiotic-resistant strains.

Despite effective reduction of the incidence of IPD caused by vaccine serotypes in both children and adults due to the usage of the current pneumococcal vaccine PCV7, the mortality rate of pneumococcal disease remains high. After the introduction of PCV7 in 2000, nonvaccine serotype 3 was found to be a significant cause for necrotizing pneumonia in children in Utah, whereas a mucoid serotype 3 was usually reported to cause lung abscess in adults. Serotype 19A has been reported the predominant serotype causing IPD all over the world. In Taiwan, complicated pneumococcal pneumonia still remains a clinically intricate problem, and its significant association with the clonal spread of CC320 within serotype 19A was noteworthy recently in Taiwan. Besides pneumococcal serotypes 3 and 19A, other nonvaccine serotypes, including 1, 5, 6A, and 7F, were also common causes for IPD around the world (Grijalva and Pelton, 2011). A second-generation 13-valent pneumococcal conjugate vaccine (PCV13) was therefore developed to address this new global issue of pneumococcal infection in 2010 (Grijalva and Pelton, 2011).

Hemolytic uremic syndrome (HUS), one of the most severe complications of IPD, mainly occurs in children, and it is also associated with hemolytic anemia, thrombocytopenia, and acute renal failure. This disorder, usually occurring in healthy young children, is one of the most common causes of acute renal failure in pediatric patients. Management of the pneumococcal HUS primarily includes an intensive antimicrobial therapy and the dialysis and transfusion of washed RBC, platelets and plasma. Most cases of HUS are reported by an acute gastroenteritis related to *Escherichia coli* (O157: H7), and often show good prognosis with recovery of renal function. However, the mortality rate of patients with pneumococcal HUS was high in early reports. Of the 14 cases recently reported from USA, 1 (7%) died and 4 (29%) developed chronic kidney disease.

*S. pneumoniae* encodes many virulence factors, but only the secreted neuraminidase A (NanA) was reported to be attributed to HUS. Neuraminidase cleaves N-acetylneuraminic acid (sialic acid) residues on red blood cells (RBC), platelets and endothelial cells, and the results may lead to the exposure of the Thomsen-Friedenrich antigen (T antigen), and allow the circulating anti-T antigen antibodies to react with the exposed T antigen on cells. The role of neuraminidase(s) in pneumococcal diseases is illustrated based on the fact that pneumococci produce two or three distinct neuraminidases, which are NanA, NanB, and NanC. All three neuraminidases have typically signal peptides for secretion, wherein NanA, unlike NanB and NanC, contains a C-terminal cell surface anchorage domain. NanA and NanB expose host cell surface receptors for pneumococcal adherence by cleaving sialic acid from the glycans and mucin of cell surface, and thereby it promotes the pneumococcal colonization on the upper respiratory tract. In in vivo study, a NanA mutant was cleared from the nasopharynx, trachea, and lungs within 12 hours postinfection, while a NanB mutant persisted but did not increase in either the nasopharynx, trachea, or lungs. However, the role of NanC remains unknown.

The nonvaccine serotypes have been emerging after the use of vaccines. Moreover, nothing worse than the fact that non-vaccine strains usually displayed increase antimicrobial resistance and virulence. This is the reason why the issue of pneumococcal infection remains to be a global public health challenge. Thus, continued efforts to develop new diagnostic methods and to develop vaccines with expanded or universal coverage, such as a universal protein vaccine, are critically required for the better control of the pneumococcal infections.

SUMMARY OF THE INVENTION

Based on our finding that *S. pneumoniae* isolates causing HUS, were mostly found to produce all of the three neuraminidases, including NanA, NanB, and NanC, we designed three primer sets to detect and clone these pneumococcal neuraminidase genes in this invention. The three recombinant neuraminidases combined together serve as an ideal vaccine candidate because it presents the best protective efficacy against pneumococcal infection in mice, compared to the others. In one embodiment, the present invention provides a method of molecular detection of pneumococcal diseases by PCR in a *S. pneumoniae*-infected sample to amplify three neuraminidase genes based on the sequences of the three neuraminidase genes of *S. pneumoniae* strain CGSP14. In another embodiment, the present invention provides a method of generating immunization in humans and animals against *S. pneumoniae* infection using a composition comprising the three recombinant neuraminidases, including NanA, NanB, and NanC.

In still another embodiment, the present invention provides protection against *S. pneumoniae* infection using three pneumococcal neuraminidases as antigens in active immunization, and/or using anti-neuraminidase antibodies for passive immunization. In a further embodiment, the present invention provides a method of detecting inhibition of a neuraminidase activity by antibody or antiserum using flow cytometry. In still a further embodiment, the present invention is able to detect the presence of any of the three neuraminidases in the *S. pneumoniae*-infected samples using the anti-neuraminidase antibodies generated from neuraminidases-immunized humanized animals.

DETAILED DESCRIPTION OF THE INVENTION

Figure 1:
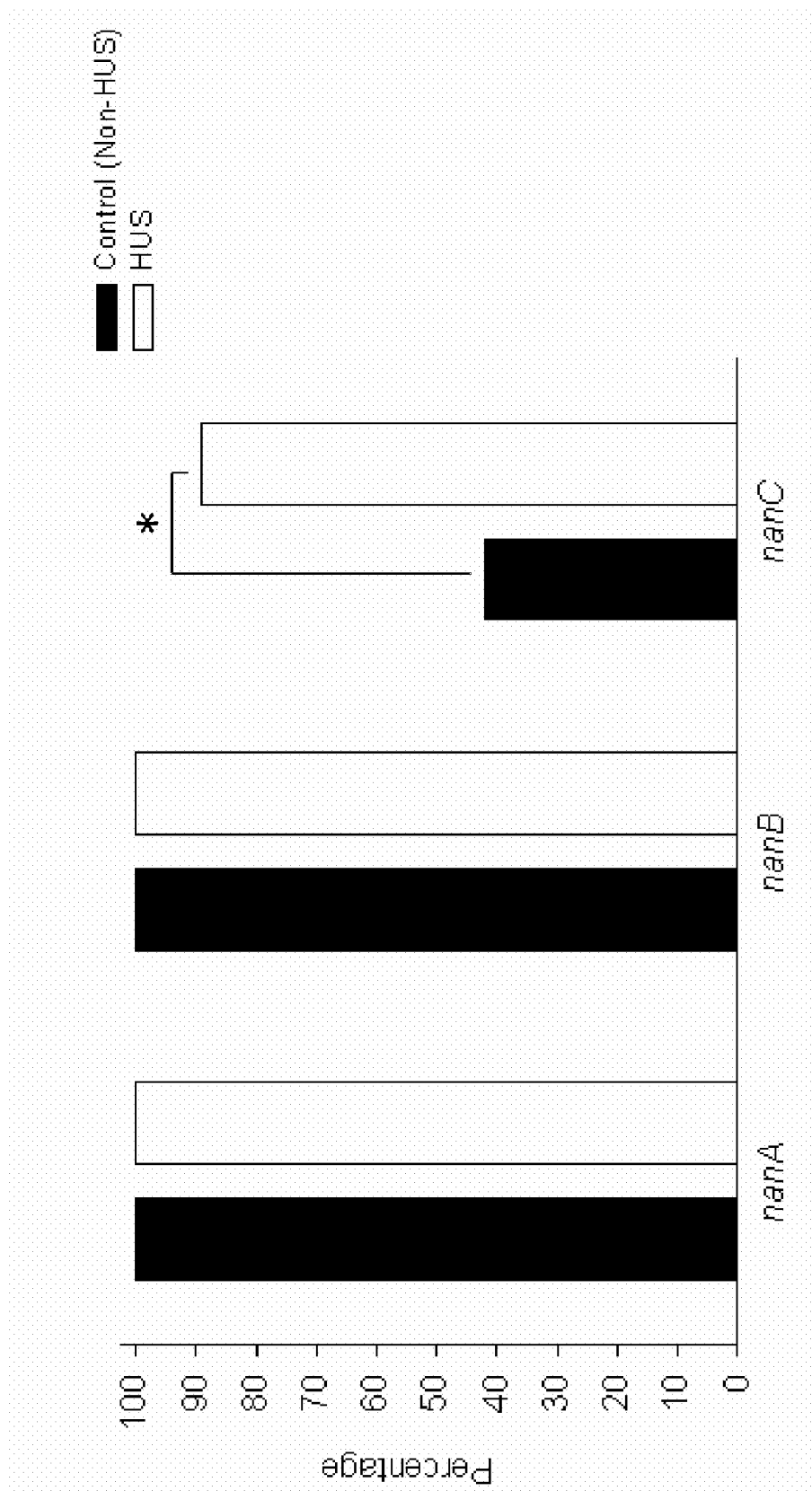
FIG. 1: Percentage of neuraminidase genes nanA, nanB and nanC among *Streptococcus pneumoniae* isolates derived from HUS patients and non-HUS controls (nanC 89% vs. 41% *p<0.005).

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

A. Detection of Neuraminidase Genes nanA, nanB and nanC of *S. Pneumoniae*

NanA and NanB have been considered to be virulence factors of *S. pneumoniae*; however, NanC remains poorly understood. The nanC gene was found in the genome of a serotype 14 strain that was isolated from a child with HUS. In this invention, we confirmed that the *S. pneumoniae* neuraminidase genes nanC as well as nanA and nanB are important virulence factors. Three primer sets for polymerase chain reaction (PCR) are designed for the detection and cloning of the neuraminidase genes that are nanA (Seq. ID No. 1), nanB (Seq. ID No. 2), and nanC (Seq. ID No. 3), based on the genomic sequence of *S. pneumoniae* strain CGSP14 with NCBI accession number NC_010582. The detection comprises those pneumococcal isolates, especially for invasive pneumococcal diseases, including HUS.

Primer Design to Amplify nanA, nanB and nanC

Three primer sets used for PCR-amplification of nanA, nanB and nanC are designed with two purposes: one is provided for gene detection, and the other for gene cloning into an expression vector as described later.

1. For nanA amplification based on Seq. ID No. 1:

```
NanA-ATG-Kpn1:
5'-AGATCTGGGTACCATGTCTTATTTCAGAA ATCG

NanA-TAA-Xho1:
5'-TGGTG CTCGA GTTGTTCTCTCTTTTTCCCT A
```

The expected size of amplicon is 2964 bp long.

2. For nanB amplification based on Seq. ID No. 2:

```
NanB-ATG-Kpn1:
5'-AGATCTGGGTACCATGAATA

AAAGAGGTCTTTA

NanB-TAA-Xho1:
5'-TGGTG CTCGA GTTTTGTTAA ATCATTAATT TC
```

The expected size of amplicon is 2115 bp long.

3. For nanC amplification based on Seq. ID No. 3:

```
NanC-ATG-Kpn1:
5'-AGATCTGGGTACCATGAAAAAAAAT

ATTAAACA

NanC-TAA-Xho1:
5'-TGGTG CTCGA GATTCTTTTTCAGATCTTCAA
```

The expected size of amplicon is 2244 bp long.

In these primer sets, the bold sequences based on the neuraminidase genes are designed for the cloning of full length of genes; the underlined sequences GGTACC and CTCGAG are the KpnI and XhoI recognition sites, respectively, which are built in for cloning into an expression vector; and the plain sequences are extra-sequences which are generated for efficient digests by KpnI and XhoI.

Detection of Neuraminidase Genes nanA, nanB and nanC in Pneumococcal Isolates

The clinical data related to *S. pneumoniae* infection from Chang Gung Memorial Hospital (CGMH), Taoyuan, Taiwan were compiled in the study of this invention. The invasive pneumococcal disease (IPD) cases are defined as the isolates of *S. pneumoniae* from normally sterile sites, such as blood, cerebrospinal fluid, or pleural fluid. Patients hospitalized with HUS, associated with an IPD between January 2006 and December 2009, were children less than 18 years old. HUS is defined according to the definition of Centers for Disease Control and Prevention (CDC, 1997). For HUS diagnosis, coagulation studies were examined, and the presence of normal fibrinogen was used to rule out disseminated intravascular coagulopathy. HUS patients enclosed were confirmed for Thomsen-Friedenrich antigen (TA) activation by the peanut (*Arachis hypogaea*) lectin agglutination method.

In our study, 18 *S. pneumoniae* isolates from patients with HUS and 54 from non-HUS patients were collected for detecting the neuraminidase genes by PCR using the primer sets designed as the above section. *S. pneumoniae* intrinsically carry nanA and nanB, as 100% of isolates from both groups have the two genes; however, relative to 16 (89%) of the HUS isolates that harbor nanC, only 22 (41%) isolates from the 54 controls carry the gene (P=0.002) (FIG. 1).

Among the total of 72 *S. pneumoniae* isolates examined in this invention, 72% (21/29) of the serotype 14 isolates contained nanC and 48% (14/29) of the patients infected by this serotype caused necrotizing pneumonia. Furthermore, 56% (5/9) of the serotype 3 isolates contained nanC and 44% (4/9) caused necrotizing pneumonia. Although 60% (6/10) of the serotype 6B and 71% (5/7) of the 23F also contained nanC, the two serotypes less commonly had necrotizing pneumonia and HUS. In contrast, 19F and its two allele MLST variant 19A seldom contained nanC (only 1 19F), but 38% (3/8) of the patients infected by 19A and 22% (2/9) by 19F had necrotizing pneumonia. The difference showed marginally significant (P=0.051) between HUS isolates and those specifically from necrotizing pneumonia patients.

Given the fact that almost all patients with HUS caused necrotizing pneumonia, the result suggests that NanC should be a virulence factor for necrotizing pneumonia as well as for HUS. We conclude that nanC gene is one of important microbe factors for necrotizing pneumonia and HUS caused by *S. pneumoniae* serotypes, not just by serotype 14 as mentioned previously.

B. Biofunctional Assays of Neuraminidase NanA, NanB And NanC of *S. pneumoniae* Strains CGSP14

In order to analyze the biofunction of neuraminidases in this invention, the recombinant NanA, NanB, and NanC of *S. pneumoniae* strains CGSP14 were cloned by using the primer sets as described in the previous section, and also characterized for their features. These biofunctional assays characterized include the exposure of the Thomsen-Friedenrich antigen (TA) and substrate specificity as the follows.

Cloning, Expression, and Purification of Recombinant NanA, NanB, and NanC

Figure 2:
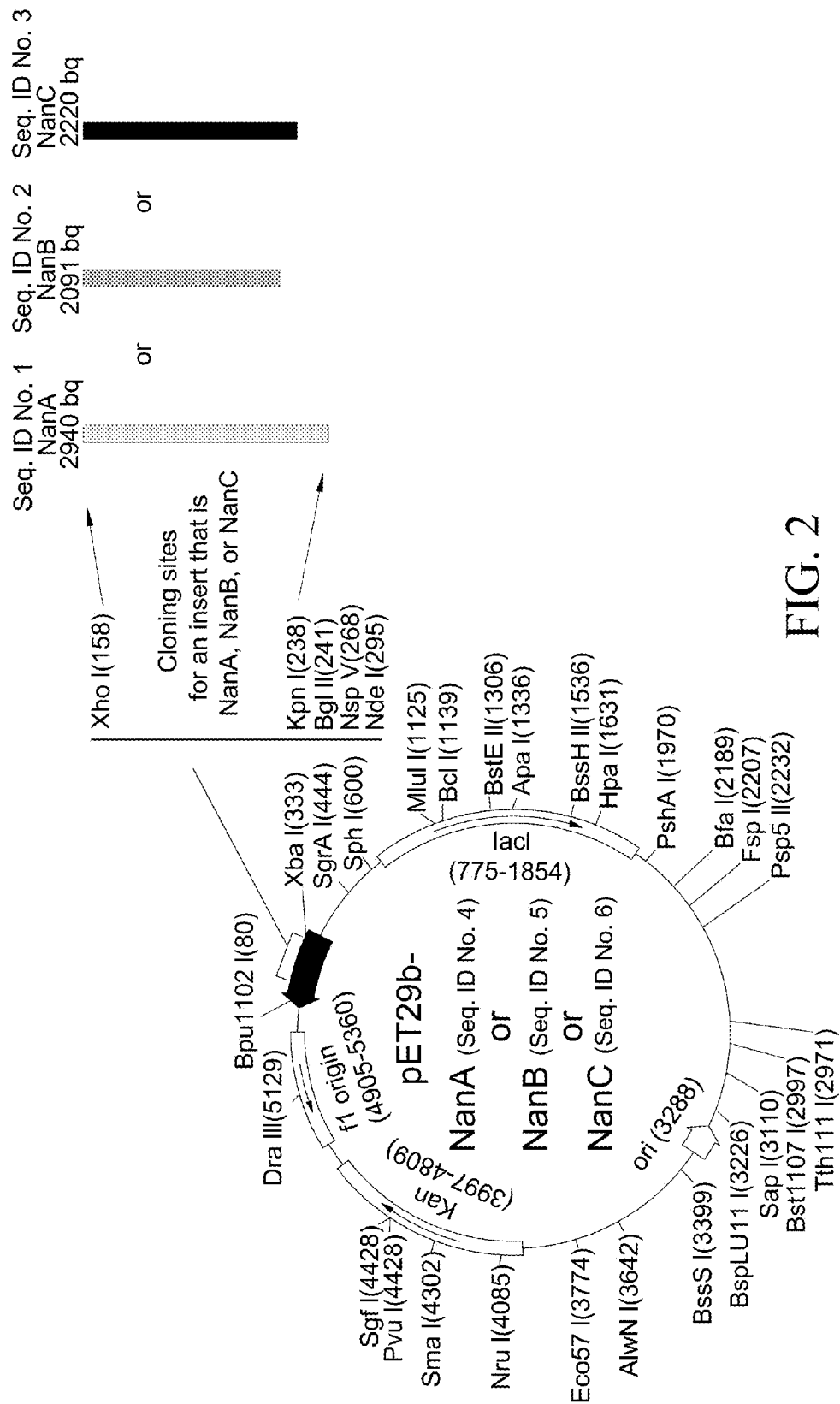
FIG. 2: Schematic diagram of the recombinant clones. Each PCR-amplified amplicon of neuraminidase genes (including nanA, nanB, and nanC), which sequences were based on the genomic sequence of *S. pneumoniae* strain CGSP14, was cloned into an expression vector pET29*b* through restriction enzyme digest by KpnI and XhoI. Seq. ID (from No. 1 to No. 6) indicates individual sequences among those genes and clones.

Referred to FIG. 2, genes nanA (Sequence ID No. 1), nanB (Seq. ID No. 2), and nanC (Seq. ID No. 3) based on the genomic sequence of *S. pneumoniae* strain CGSP14 with NCBI accession number NC_010582 were PCR-amplified and cloned into the expression vector pET29b (NOVAGEN, MERCK, Darmstadt, Germany) using KpnI and XhoI as cloning sites; the resulting clones are pET29b-NanA (Seq. ID No. 4), pET29b-NanB (Seq. ID No. 5), and pET29b-NanC (Seq. ID No. 6), respectively. The recombinant proteins, thus, can be inducibly over-expressed by the supplement of isopropyl 13-D-1-thiogalactopyranoside (IPTG, 1 g/mL) in any Gram-negative bacteria, such as *Escherichia coli* BL21 (DE3). *E. coli* clones were cultured in Luria-Bertani (LB) broth at 37° C. for 4 hours with IPTG induction, where the original culture was 1/100 dilution with LB broth prior to IPTG induction. Because the recombinant NanA, NanB and NanC are histidine-tagged fusion proteins with the sizes of 100, 80, and 85 kDa, respectively, they may be easily purified according to the manufacturer's instructions for any kinds of $Ni^{2+}$ affinity chromatography, such as Nickel-Chelating Resin (Invitrogen, Carlsbad, Calif., USA).

TA Exposure Activities on Cells Used to Confirm the Features of Recombinant NanA, NanB and NanC Referred to FIGS. 3A-3D, the TA exposure activities of the recombinant neuraminidases were tested.

Lectins are usually used to recognize glycoconjugate residues (such as TA antigen) on cells. Fluorescein-labeled peanut agglutinin (PNA; Vector Laboratories, Inc., Burlingame, Calif. 94010, U.S.A.) is commonly used to detect TA on cells. Fluorescein-labeled *Sambucus Nigra* lectin (SNA; Vector Laboratories, Inc., Burlingame, Calif. 94010, U.S.A.) and biotinylated *Maackia Amurensis* lectin II (MAL II; Vector Laboratories, Inc., Burlingame, Calif. 94010, U.S.A.) are applied to recognize α2-6 and α2-3 sialyl linkages, respectively.

For the detection of the glycoconjugates on red blood cell (RBC), freshly collected blood samples from healthy volunteers were used to prepare the RBC fraction according to the method described in AABB Technical Manual, 14th Edition (http://freetechebooks.com/ebook-2011/aabb-technical-manual.html). RBC ($3\times10^7$ cells/mL), A549 (human epithelial lung cell line; ATCC® Number: CCL-185™) and HK-2 (human kidney 2 cell line; ATCC® Number: CRU-2190™) cells ($1\times10^6$ cells/mL) were cultured in Dulbecco's modified Eagle's medium (DMEM) plus Ham F12 medium, and treated with neuraminidase NanA, NanB or NanC (1 μg for RBC; 0.1 μg for A549 and HK-2). The mixture was incubated at 37° C. for 1-2 hours. For flow cytometric (FACScan, Becton Dickinson, USA) analysis, 10,000-20,000 cells were used, and cell labeling with each of lectins, including PNA, SNA and MAL II was done at 4° C. for one hour, rather than higher temperature (such as 37° C.) and longer time period (such as overnight) to cause cell agglutination, which would jam flow analysis. Biotinylated MAL II labeling can be observed by using fluorescein-conjugated streptavidin. Furthermore, to observe for cell agglutination by microscopy, 20 μl aliquots of lectin-labeled RBC were incubated at 37° C. for 30 minutes.

Figure 3A:
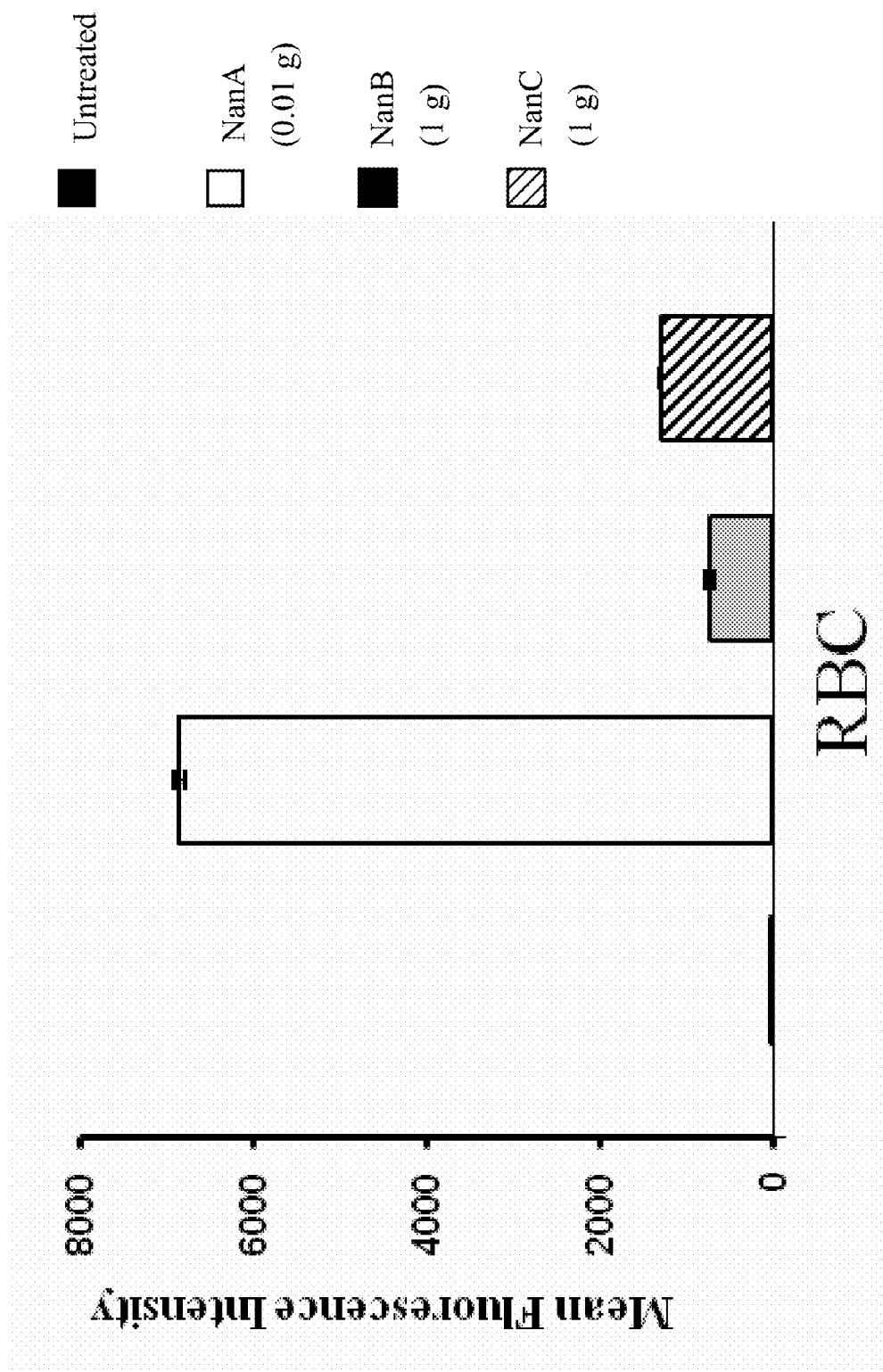
FIGS. 3A-3D: Thomsen-Friedenrich antigen (TA) exposure on cells. PNA lectin binding was used to detect the TA by flow cytometry. Numbers indicate fluorescence counts of samples, which are untreated cells (black), NanA-treated (white), NanB-treated (grey), and NanC-treated (hatched). NanA (0.01 µg), NanB (1 µg) and NanC (1 µg) can expose TA on RBC (Figure A). NanA, NanB and NanC (all were 1 µg) can expose TA on A549 (Figure B) and HK-2 cells (Figure C). Twenty 4 aliquots of PNA lectin labeled RBC used for flow cytometric analysis were incubated at 37° C. and observed under microscope to verify agglutination. Agglutination of RBC was observed when treated with NanA, NanB and NanC (0.1 µg) (Figure D).
Figure 3B:
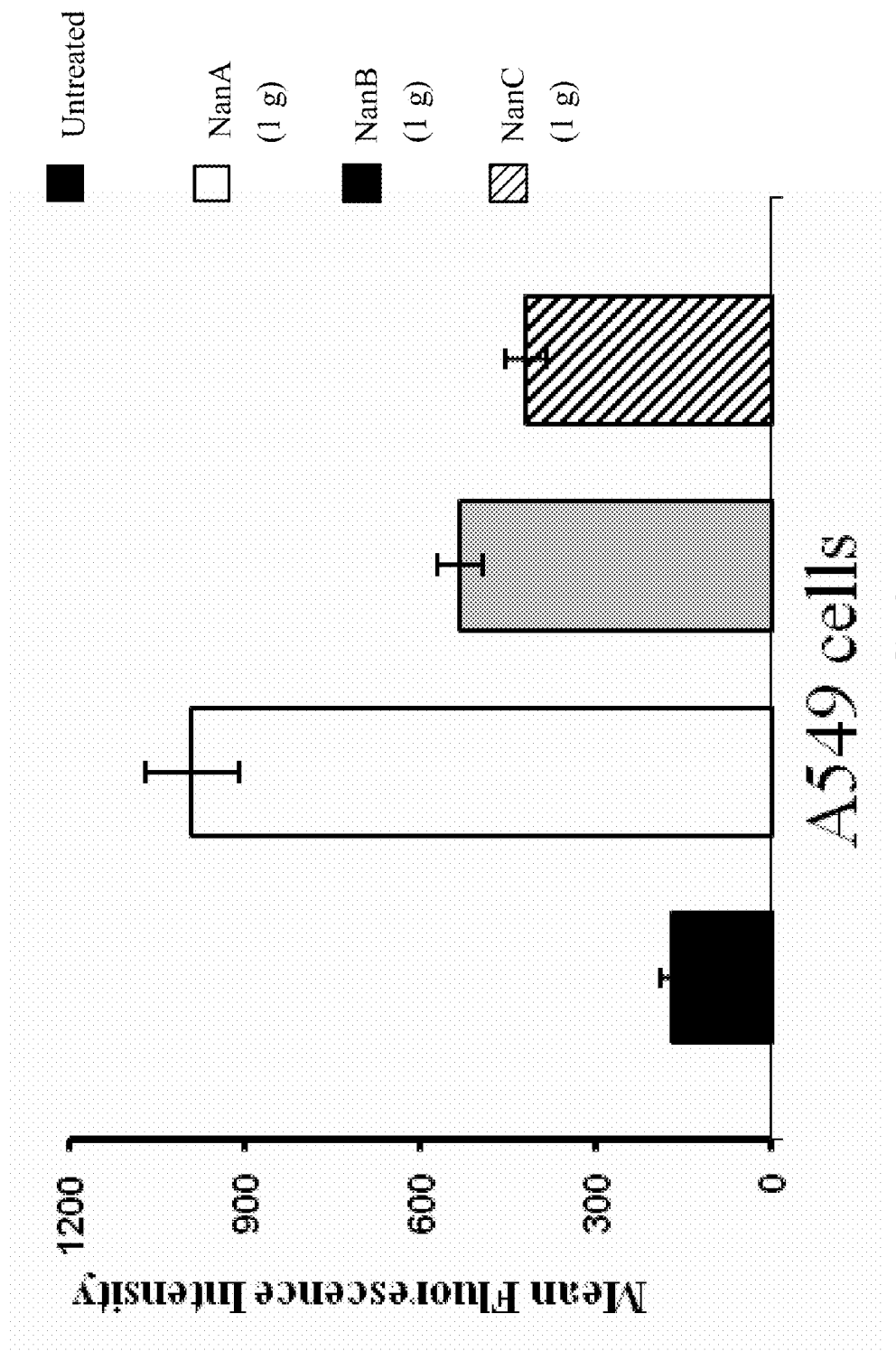
Figure 3C:
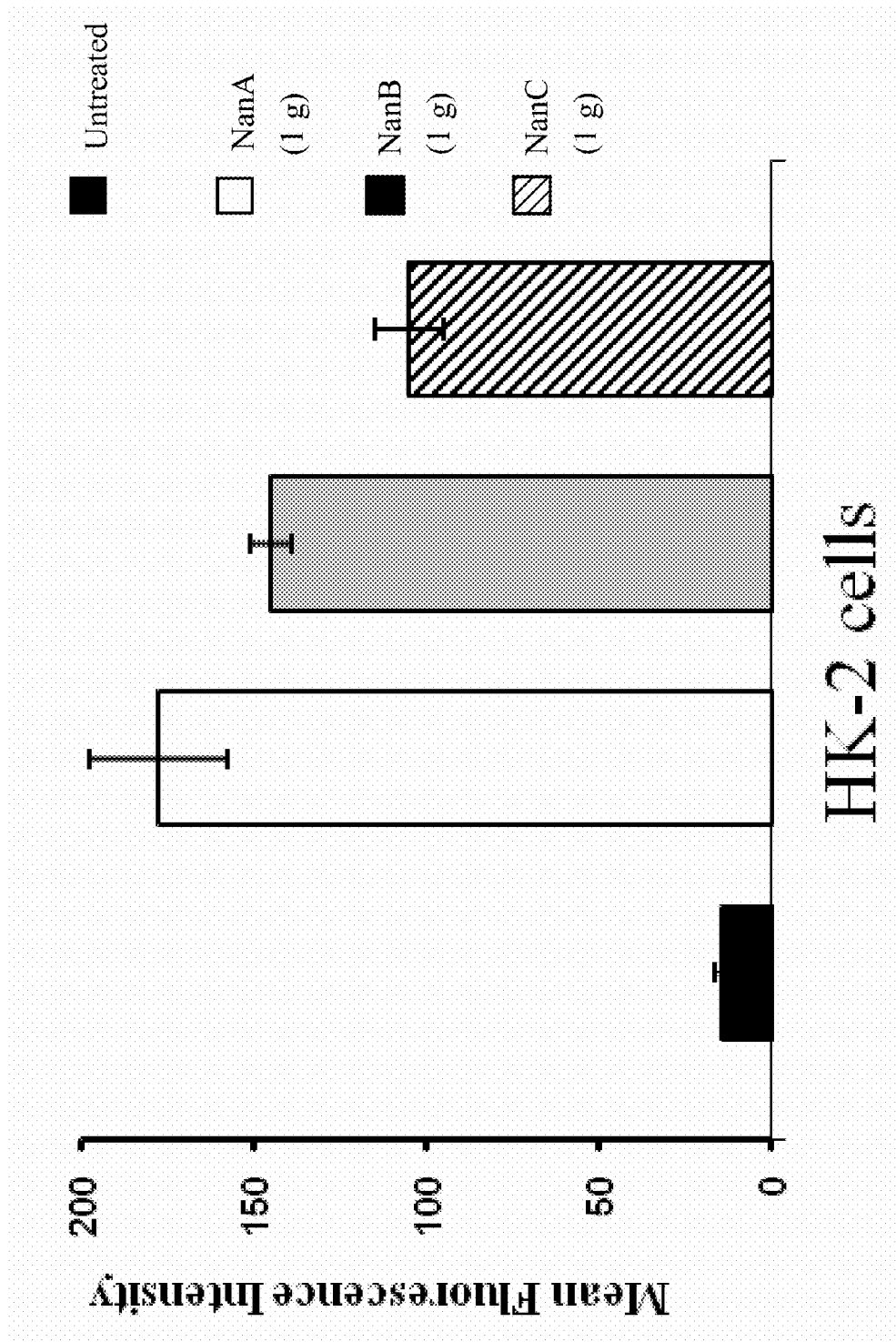
Figure 3D:
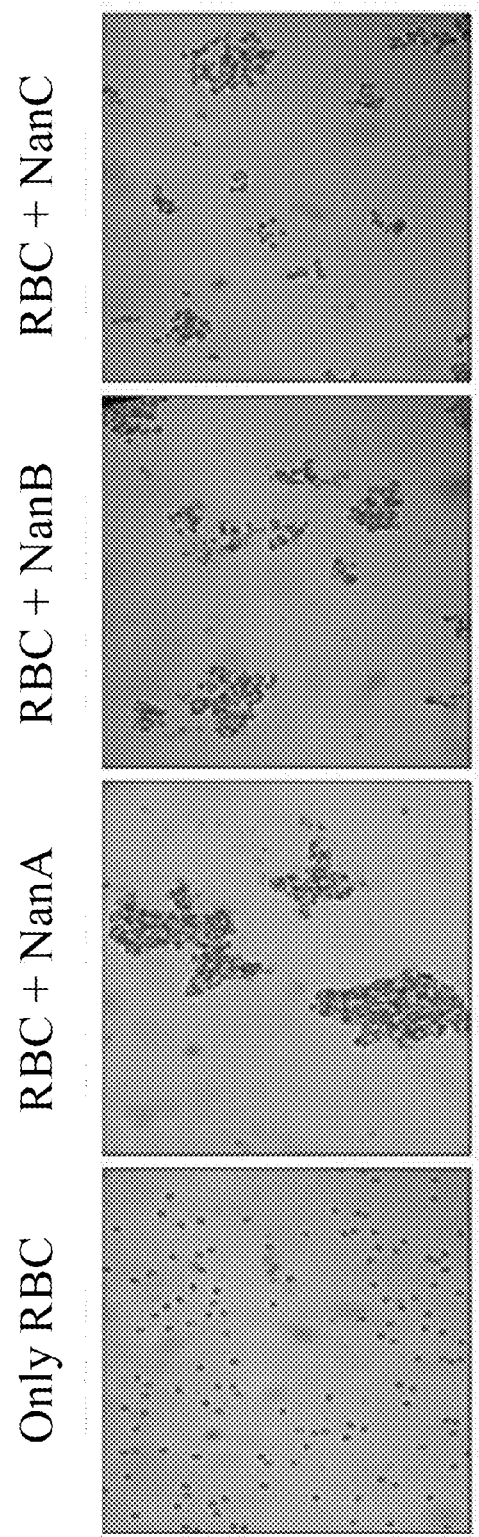

As shown in a previous report, TA exposure on RBC, platelets and glomeruli is mediated by the secreted NanA in pneumococcal infection. To proof whether NanC was also a potential virulence factor associated with HUS, the ability of NanC was analyzed to expose TA on cells. When RBC, A549 and HK-2 cells were treated with the recombinant NanB and NanC, TA exposure was detected (FIGS. 3A, 3B, and 3C). On RBC, the TA exposure activity of NanA had shown to reach a plateau when NanA used was more than 0.01 μg. Thus, 0.01- μg NanA was used to compare with 1-μg NanB and 1-μg NanC. The results showed that the activity of NanA was $9.4\times10^2$ and $5.3\times10^2$ times higher than those of NanB and NanC, respectively. When lectin-PNA was used to verify TA exposure on RBC, NanA-treated RBC showed larger aggregates under microscopic examination, compared to the treatments by NanB and NanC (FIG. 3D), whereas no agglutination was present with PNA in the case of untreated RBC. NanA activity shown on A549 cells was 2.2 and 3.3 times higher than NanB and NanC, respectively, while NanA activity on HK-2 cells was 1.5 times higher than both NanB and NanC.

C. Protection by Immunization Using Recombinant NanA, NanB, and NanC as Antigens In order to develop an ideal vaccine against pneumococcal infection, particularly to be a universal protein vaccine, we chose three pneumococcal neuraminidases as a vaccine material to immunize mice, while PPV23 vaccine was used as a positive control. Meanwhile, the neuraminidase-immunized antisera were also applied for the inhibition assay against the neuraminidase activity.

Vaccination Against *S. pneumoniae* in Mice

Figure 4:
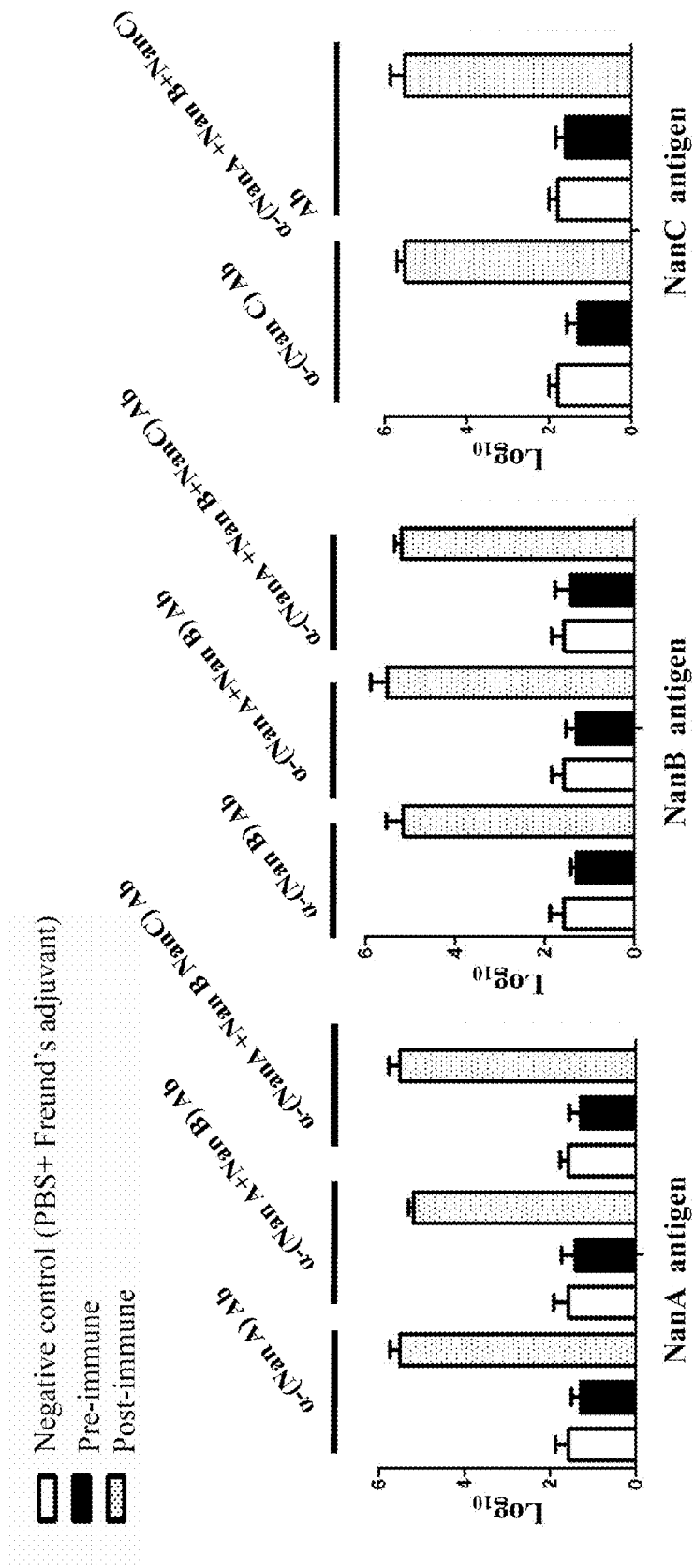
FIG. 4: Confirmation of mouse polyclonal antisera against neuraminidase(s) by enzyme-linked immunosorbent assay (ELISA). Mouse post-immune (grey box) antisera against neuraminidase(s) antigens from different combinations, including individual neuraminidase (NanA, NanB, or NanC), neuraminidase A+B (NanA+NanB), and neuraminidase A+B+C (NanA+NanB+NanC), were tested by ELISA, while the sera from pre-immune (black box) and negative control (only PBS plus Freund's adjuvant without antigen; white box) were also examined. The antigen-antibody interactions were quantified by using the peroxidase-conjugated goat anti-mouse IgG (Sigma) as a secondary antibody and tetramethylbenzidine/peroxide (R&D Systems, Minneapolis, Minn., USA) as a color-developing substrate under the analysis of ELISA reader with the maximum absorbance band at a wavelengthh of 405 nenometer (EMax, Molecular Devices, Sunnyvale, Calif. 94089 USA). The value was presented by the logarithm of the value on y-axis.
Figure 5:
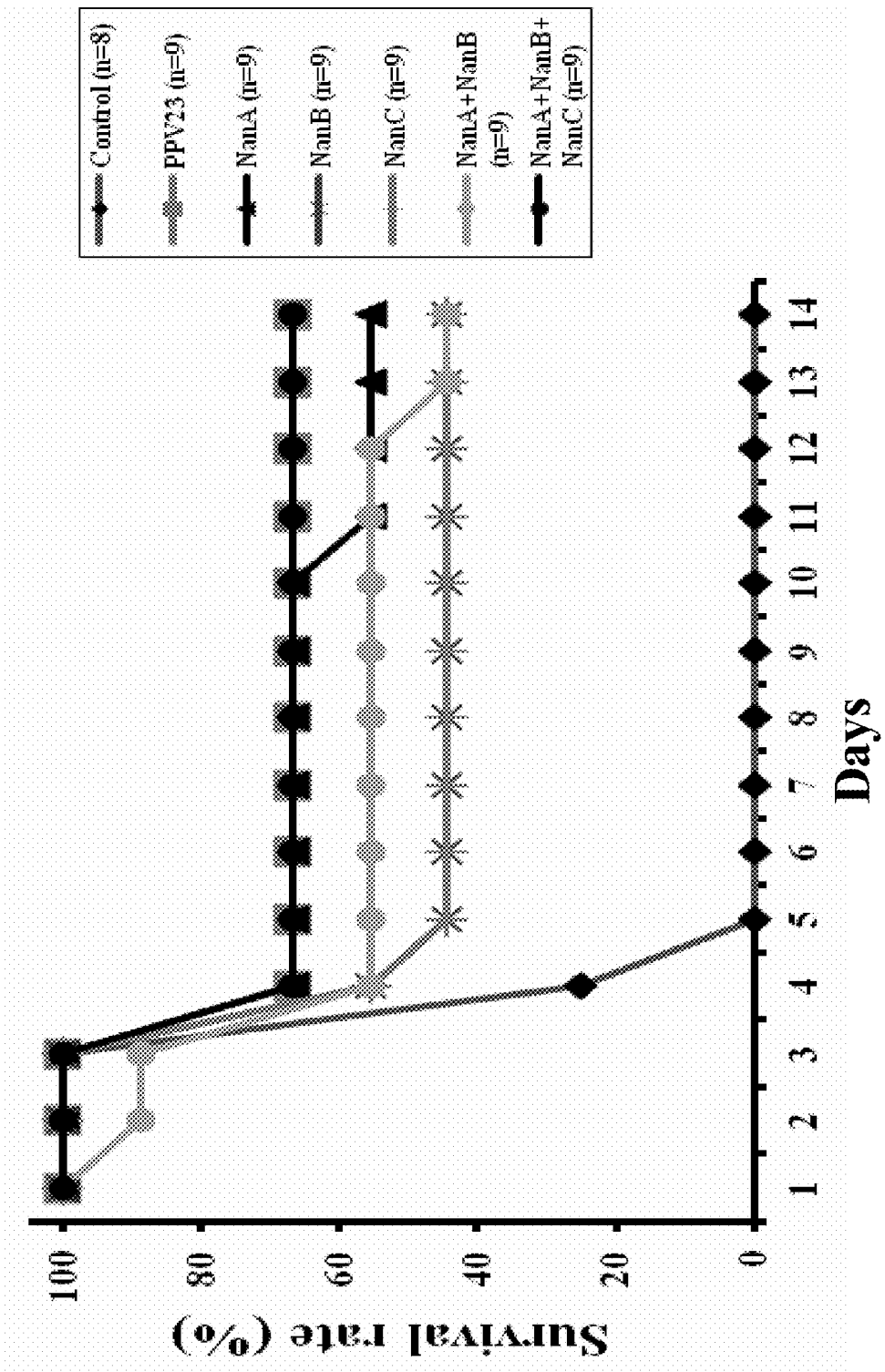
FIG. 5: Vaccination tests. The individual or combination of three neuraminidases, NanA, NanB and NanC with 10 µg of each enzyme, were applied as antigens to immunize mouse (BALB/C, one month old) four times at 2-week interval, while PPV23 vaccine and a negative control (PBS+Freund's adjuvant) were taken for comparison. Thereafter, *S. pneumoniae* serotype 3 ($3 \times 10^3$ cfu) was used to challenge those neuraminidase-immunized mice. Freund's complete adjuvant for the first time immunization and Freund's incomplete adjuvant for the last three immunizations were used with the ratio of 1:1 to the antigen(s). Mice survival rate (%) was determined during 14 days feeding after four times neuraminidase immunization and a subsequent *S. pneumoniae* challenge. N is the number of mice for test.

Referred to FIGS. 4 and 5, the recombinant NanA, NanB and NanC were used as the antigens to protect the mice against *S. pneumoniae* in mice in this invention. For comparison of vaccination, the individual or combination of neuraminidases NanA, NanB and NanC (10 µg/each enzyme) were applied to immune mice (BALB/C, one month old) four times at 2-week interval prior to *S. pneumoniae* ($3 \times 10^3$ cfu) challenge, while 23-valent Pneumovax® (Merck Sharp & Dohme Corp., NJ08889, USA) polysaccharide vaccine (PPV23) and only phosphate buffered saline (PBS) were used as positive and negative controls, respectively. Freund's complete adjuvant for first time immunization and Freund's incomplete adjuvant for the last three immunizations were used with the ratio of 1:1 to the antigen(s).

To confirm the efficacy of mouse polyclonal anti-neuraminidase(s) antisera which were immunized by neuraminidase(s), we performed enzyme-linked immunosorbent assay (ELISA) which is based on the antigen-antibody sandwich principle. For ELISA test, the neuraminidase was first coated on an ELISA plate (Corning Incorporated, Corning, N.Y., USA). The anti-neuraminidase antiserum raised from mouse was then added to test how much antiserum was able to specifically bind on ELISA plate, and the antigen-antibody interaction was quantified by goat HRP-conjugated antimouse immunoglobulin G (IgG) as a secondary antibody (Millipore, Billerica, Mass. 01821, USA) and TMB/peroxide (R&D Systems, Minneapolis, Minn., USA) as a color-developing substrate. The post-immune antisera against neuraminidase(s) from different groups of combinations were tested, while the control sera from the pre-immune and the negative control with only PBS plus Freund's complete/incomplete adjuvants were also examined (FIG. 4). The value of antigen-antibody interaction was measured and presented logarithmically, as shown in FIG. 4. The results showed that each value of neuraminidase-immunized antisera, compared to the control sera, was 3-4 logarithm folds increase, revealing that each of three neuraminidases is an ideal antigen for immunization (FIG. 4).

For development of mouse vaccine against *S. pneumoniae*, the individual or combination of three neuraminidases, NanA, NanB and NanC with 10 µg of each enzyme, were applied to immunize nine mice (BALB/C, one month old) four times at 2-week interval, while PPV23 vaccine and a negative control (PBS+Freund's adjuvant) were taken for comparison. Thereafter, *S. pneumoniae* serotype 3 ($3 \times 10^3$ cfu) was used to challenge those immunized mice (FIG. 5). Freund's complete adjuvant for the first time immunization and Freund's incomplete adjuvant for the last three immunizations were used to mix with the antigen(s) with the ratio of 1:1. Mouse survival rate (%) was determined during 14 days of feeding after four times neuraminidase immunization and a following challenge using *S. pneumoniae* serotype 3. As shown in FIG. 5, vaccination tests showed that the group with the combination of three neuraminidases (NanA+NanB+NanC) presented the same 67% survival rate as that using the PPV23 vaccine, which value was the highest when compared to the other groups with one or two of three neuraminidases. In this invention, the combination containing three neuraminidases (NanA, NanB, and NanC) together was evaluted to be the best vaccine candidate for vaccination against *S. pneumoniae* infection in mice, and it also would be an appropriate candidate as a kind of universal protein vaccine.

Inhibition of Neuraminidase Activity by Antibodies or Immunized Antisera

As referred to FIGS. 6A to 7C, the inhibition assay was taken to test how efficient the neuraminidase activity can be inhibited by neuraminidase-specific antisera. The antisera against individual neuraminidase (NanA, NanB or NanC) were raised from rabbits, and then tested for their inhibitory effect on the activities of neuraminidases. NanC antiserum was purified by Protein A Sepharose beads (GE Healthcare) to increase its inhibition efficiency. Different amounts of neuraminidases in 10-µL PBS were pre-incubated with 10-µL immunized serum for 5 minutes. The antiserum-treated neuraminidase was mixed with RBC cells ($4 \times 10^6$ cells/mL) for 2 hours of incubation at 4° C. Inhibition of neuraminidases (NanA, NanB, and NanC) activity by rabbit antisera was quantified by TA exposure on RBCs using flow cytometry, wherein the detection of TA exposure on RBC cells using FITC-labeled PNA lectin was described in previous section. If neuraminidase is neutralized by a specific anti-neuraminidase serum, the exposure of TA antigen on RBC cells, and the value of fluorescence intensity will be reduced.

Figure 6A:
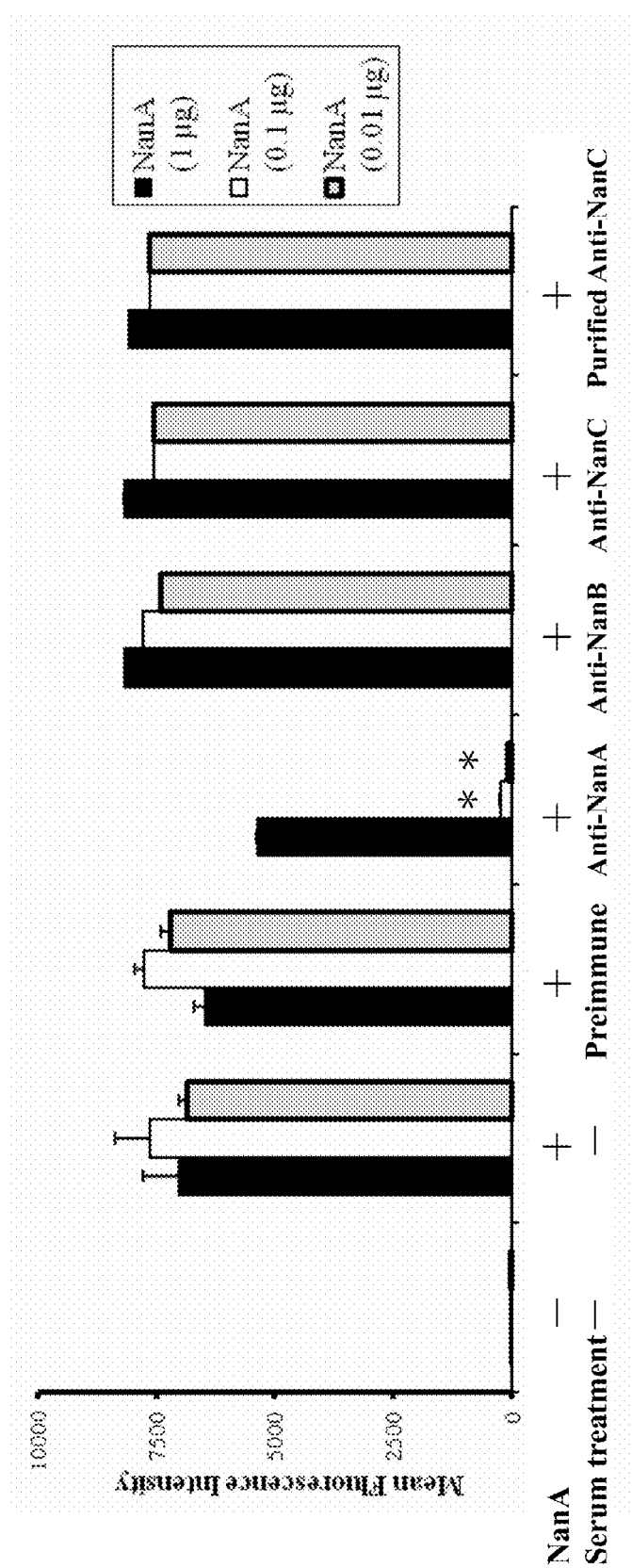
FIGS. 6A-6C: Inhibition of neuraminidase activity by the anti-serum raised from neuraminidase-immunized rabbit. Neuraminidase-mediated TA antigen exposure presented on RBC cells was quantified by flow cytometry analysis, where FITC-labeled PNA lactin was used for the recognition of TA antigen. Prior to the quantification of TA exposure, an individual neuraminidase (including NanA, NanB, and NanC) was individually added for the treatment with different anti-neuraminidase anti-sera (30 µg/mL), including purified anti-NanC antiserum. (Figure A) NanA added for the treatment of rabbit anti-neuraminidase anti-serum were 1 µg (black bars), 0.1 µg (white bars), and 0.01 µg (grey bars). (Figure B) NanB added for the treatment of rabbit anti-NanB anti-serum was 1 µg (white bars). (Figure C) NanC added for the treatment of rabbit anti-NanC anti-serum was 1 µg (grey bars). * indicates $p<0.05$, when compared to the controls (only neuraminidase addition without serum treatment; neuraminidase addition with pre-immune serum treatment).
Figure 6B:
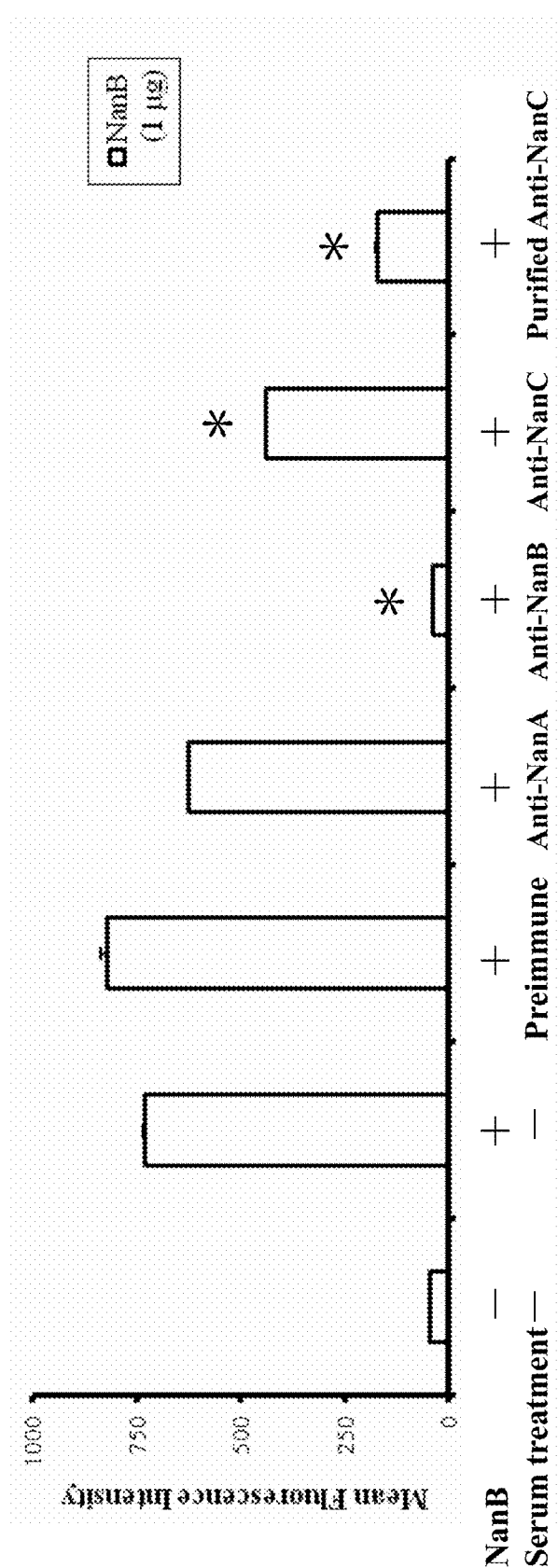
Figure 6C:
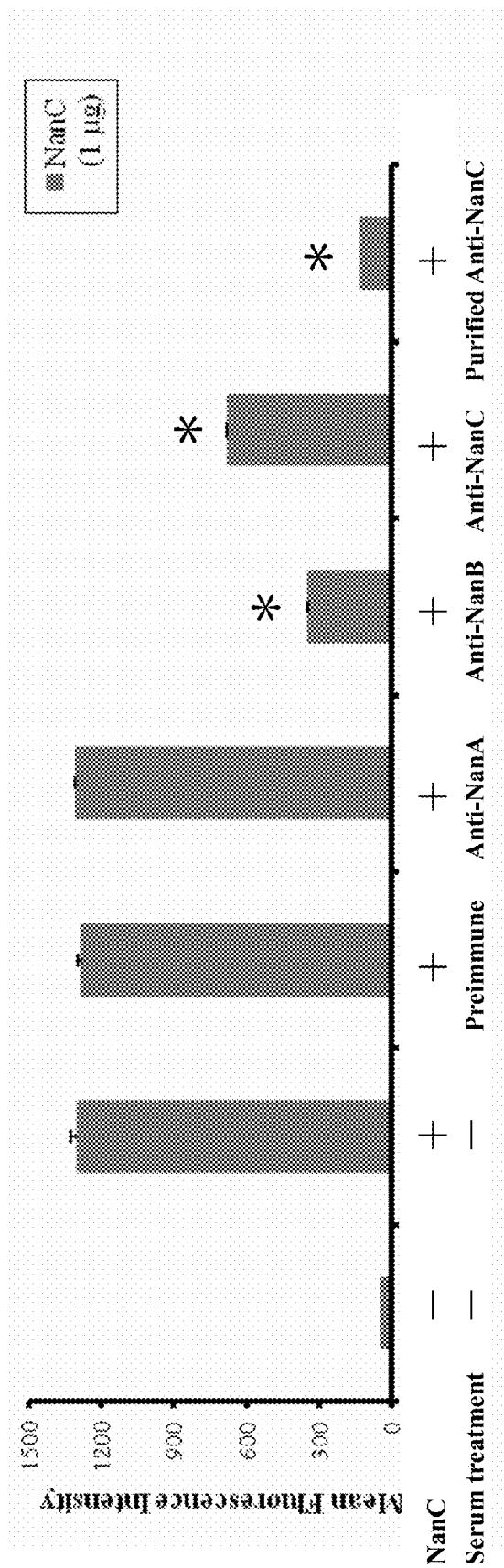

As shown on y-axis of FIGS. 6A-6C, the activities of NanB and NanC for TA antigen exposure were naturally weaker than that of NanA. NanA activity was completely inhibited by 30-µg anti-NanA antiserum when both 0.1-µg and 0.01-µg NanA were used, while only 20% activity was inhibited when 1-µg NanA was used (FIG. 6A). The 1-µg NanB activity was completely inhibited by 30-µg anti-NanB antiserum. However, only 40% NanC activity was inhibited by 30-µg anti-NanC antiserum, but 90% NanC activity was inhibited by 30-µg purified anti-NanC antiserum (FIG. 6C).

For cross-reactivity, antineuraminidase (including NanA, NanB and NanC) antisera were tested. Anti-NanA antiserum did not show inhibitory effect on the activity of NanB and NanC and vice versa. However, anti-NanB antiserum could inhibit NanC activity by 74%. Non-purified and purified anti-NanC antisera inhibited NanB activity by 40% and 76%, respectively.

The antisera from rabbit used to inhibit 50% neuraminidase activity were also assessed by titration test (data not shown). The dilution of anti-NanA antiserum for 50% NanA inhibition was 1, 8, and 32 for 1 µg, 0.1 µg and 0.01 µg, respectively. 50% NanB (1 µg) activity with anti-NanB antiserum was inhibited by 16 folds of dilution. The dilutions of non-purified and purified anti-NanC antisera to inhibit 50% NanC (1 µg) activity were 1 and 8, respectively.

Figure 7A:
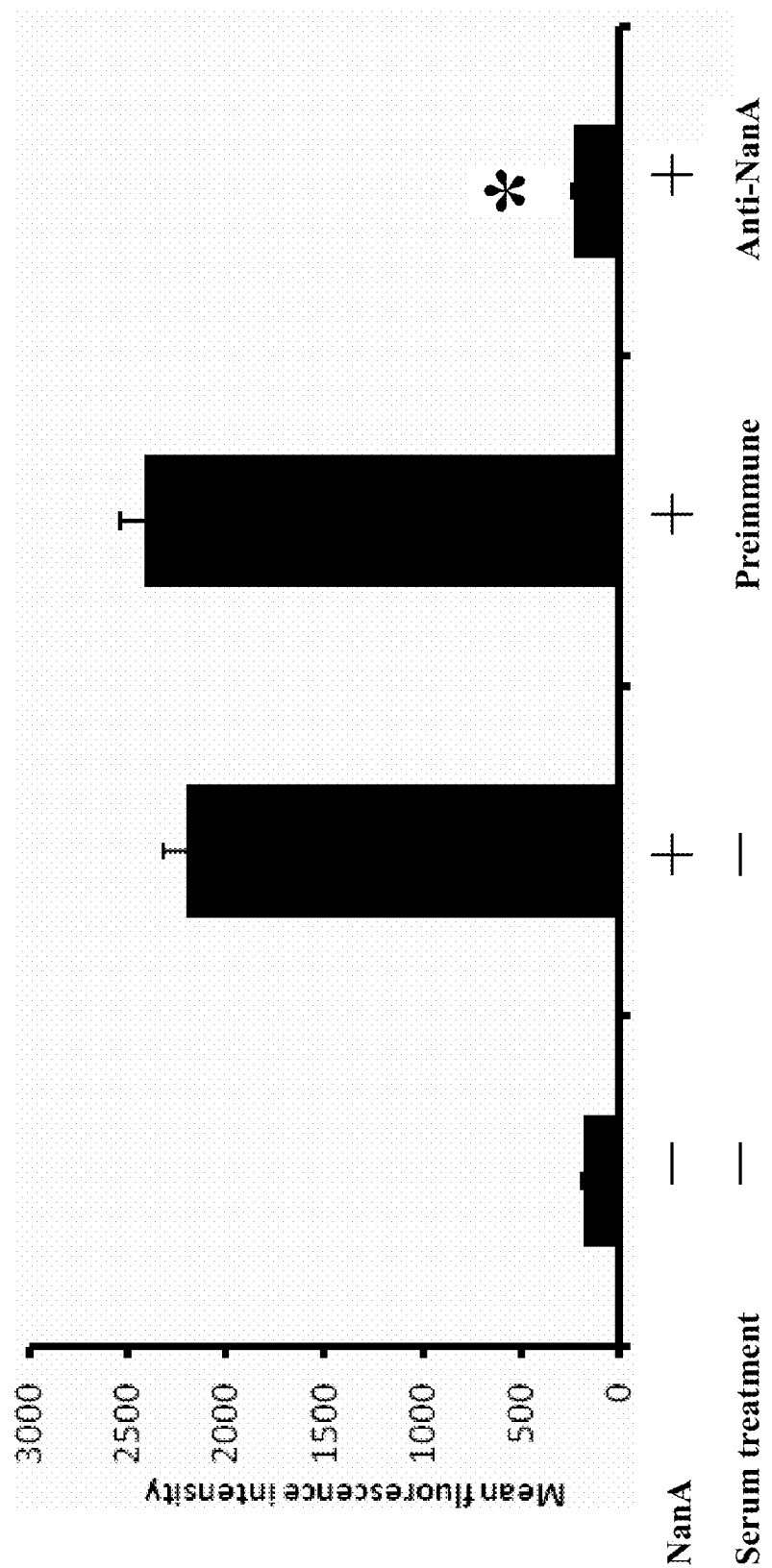
FIGS. 7A-7C: Inhibition of neuraminidase activity by the anti-serum raised from neuraminidase-immunized mouse. Neuraminidase-mediated TA antigen exposure presented on RBC cells was quantified by flow cytometry analysis, where FITC-labeled PNA lactin was used for the recognition of TA antigen. Prior to the quantification of TA exposure, an individual neuraminidase (including NanA, NanB, and NanC) was added for the treatment with specific anti-neuraminidase anti-sera (30 µg/mL). (Figure A) NanA added for the treatment of mouse anti-NanA anti-serum was 0.1 µg. (Figure B) NanB added for the treatment of mouse anti-NanB anti-serum was 1 µg. (Figure C) NanC used for the treatment of mouse anti-NanC anti-serum was 1 µg. * indicates $p<0.05$, when compared to the controls (only neuraminidase addition without serum treatment; neuraminidase addition with pre-immune serum treatment).
Figure 7B:
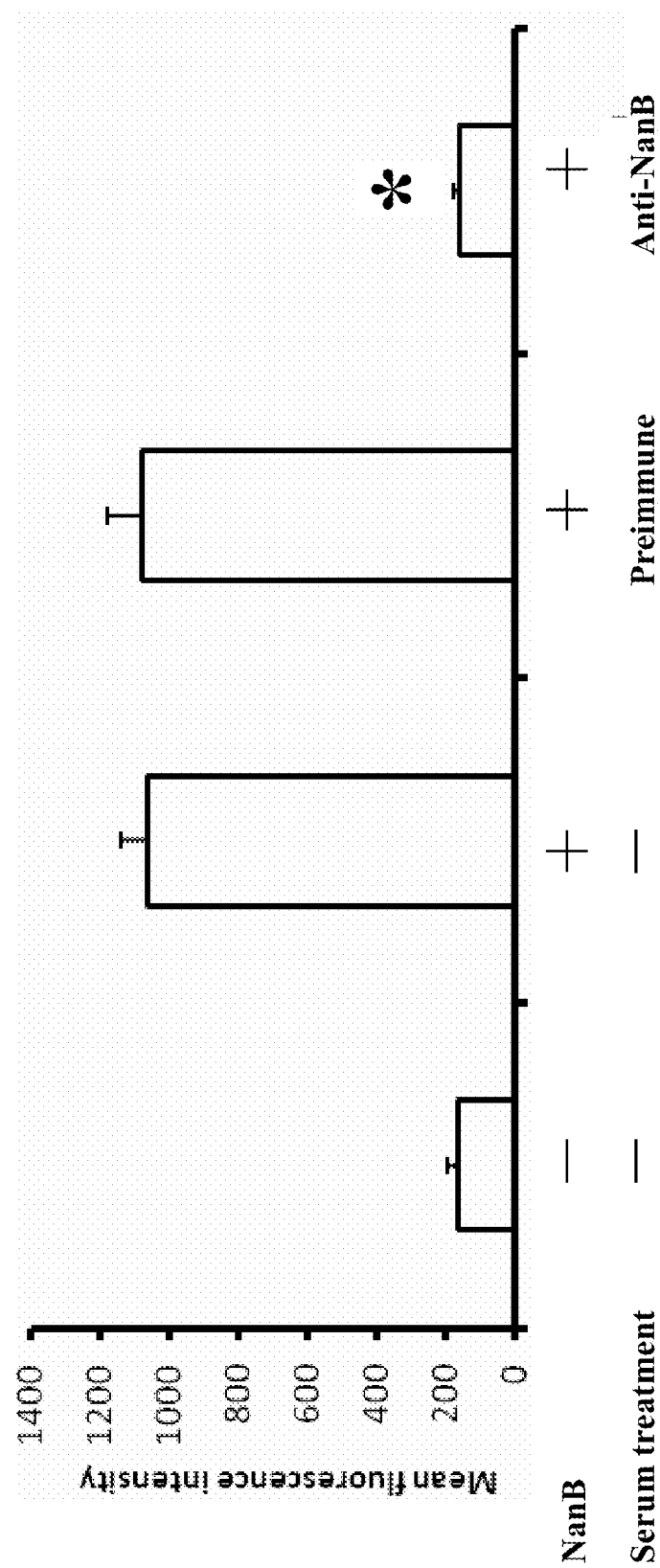
Figure 7C:
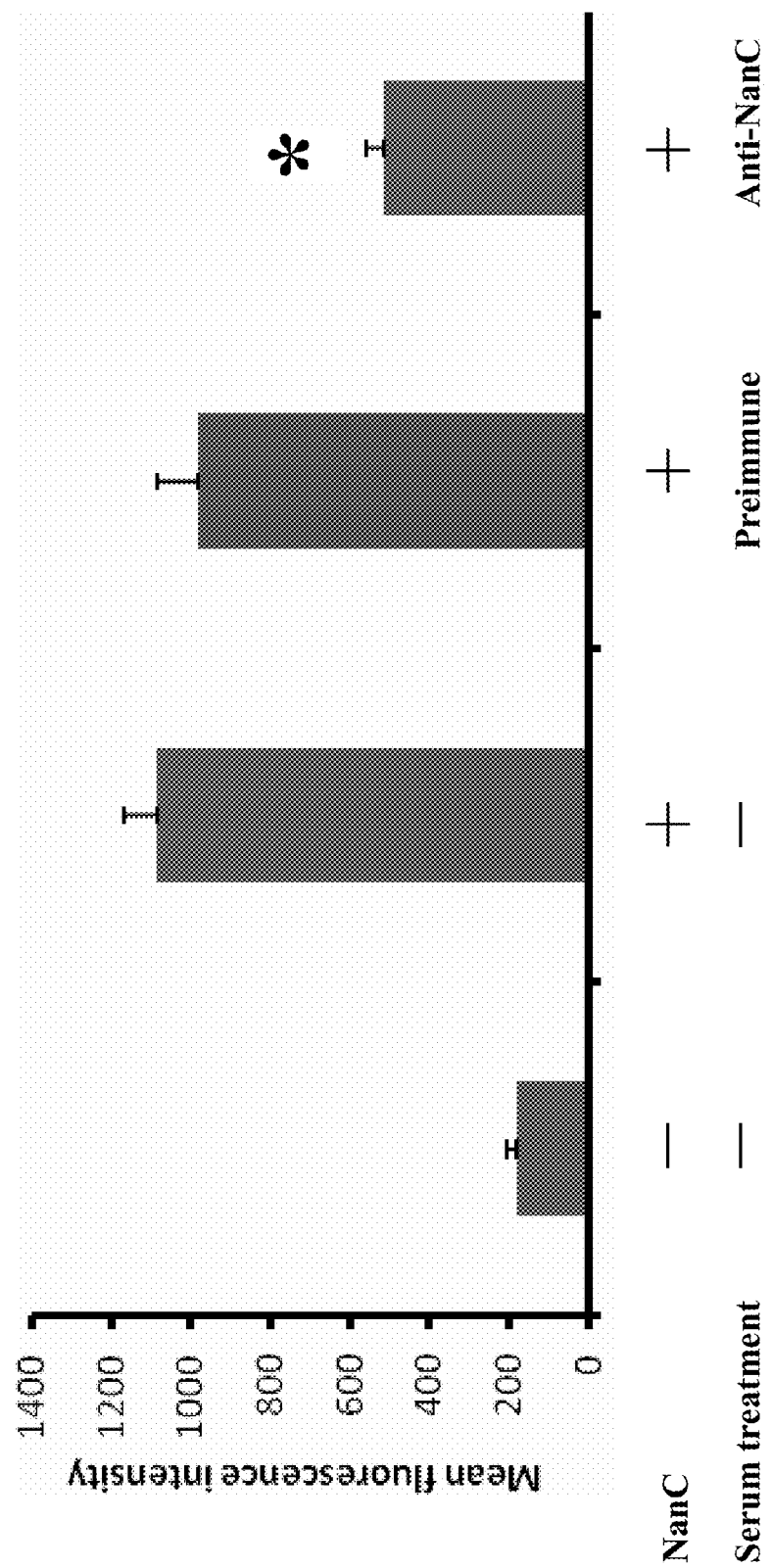

Similar to the rabbit antineuraminidase antisera, the antineuraminidase antisera raised from mouse were also shown to specifically inhibit neuraminidase activities, as shown in FIGS. 7A-7C. The 30-µg mouse Anti-NanA and anti-NanB antisera enable to completely inhibit the activities of 0.1-µg NanA and 1-µg NanB, respectively. However, anti-NanC antiserum (30-µg) was only able to neutralize 50% NanC (1-µg) activity.

Taken together, the results indicated that each of anti-neuraminidase antisera raised from both rabbit and mice enables to specifically inhibit or neutralize its corresponding neuraminidase activity; however, only anti-NanB and anti-NanC antisera have cross-protection abilities against each other. Although the inhibition of the anti-NanC antiserum was not as efficient as those anti-NanA and anti-NanB antisera, the combination of NanC with NanA and NanB is the best candidate as a vaccine.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A method of providing protection against pneumococcal infection in a subject comprises steps of:
    administering immunogenic amount of composition that includes the combination of three recombinant pneumococcal neuraminidases: NanA, NanB, and NanC of *Streptococcus pneumoniae* to the subject;
    wherein the recombinant pneumococcal neuraminidase NanA is SEQ ID NO: 4;
    wherein the recombinant pneumococcal neuraminidase NanB is SEQ ID NO: 5;
    wherein the recombinant pneumococcal neuraminidase NanC is SEQ ID NO: 6;
    wherein administering the recombinant pneumococcal neuraminidases elicits an immune response to *Streptococcus pneumoniae*.

2. The method of providing protection against pneumococcal infection in a subject of claim 1, further comprises a step of adding adjuvants to enhance the immune response.

3. The method of providing protection against pneumococcal infection in a subject of claim 1, wherein said *Streptococcus pneumoniae* includes all kinds of *Streptococcus pneumoniae* serotypes.

4. The method of providing protection against pneumococcal infection in a subject of claim 1, wherein the subject is human.

5. The method of providing protection against pneumococcal infection in a subject of claim 1, wherein the subject is animal.

* * * * *